(12) United States Patent
Dissing et al.

(10) Patent No.: US 6,561,968 B1
(45) Date of Patent: May 13, 2003

(54) METHOD AND AN APPARATUS FOR STIMULATING/ MODULATING BIOCHEMICAL PROCESSES USING PULSED ELECTROMAGNETIC FIELDS

(75) Inventors: Steen Dissing, Charlottenlund (DK); Mogens Unden, Hornbaek (DK); Teddy Hebo Larsen, Hvidovre (DK); Soren Schou, Holte (DK); Hans Nissen Petersen, Lynge (DK)

(73) Assignee: BioFields ApS, Copenhagen (DK)

( * ) Notice: Subject to any disclaimer, the term of this patent is extended or adjusted under 35 U.S.C. 154(b) by 0 days.

(21) Appl. No.: 09/650,044

(22) Filed: Aug. 29, 2000

Related U.S. Application Data

(60) Provisional application No. 60/157,042, filed on Oct. 1, 1999.

(30) Foreign Application Priority Data

Aug. 31, 1999 (DK) ......................................... 1999 01207

(51) Int. Cl.[7] ................................................. A61N 2/02
(52) U.S. Cl. ......................................................... 600/13
(58) Field of Search ...................................... 600/9–15

(56) References Cited

U.S. PATENT DOCUMENTS

| | | | | |
|---|---|---|---|---|
| 882,699 | A | * 3/1908 | Latshaw | 47/65.7 |
| 3,915,151 | A | * 10/1975 | Kraus | 600/13 |
| 4,226,246 | A | * 10/1980 | Fragnet | 607/66 |

(List continued on next page.)

FOREIGN PATENT DOCUMENTS

| | | |
|---|---|---|
| DE | 3403786 A 1 | 8/1985 |
| EP | 0 709 115 A1 | 5/1996 |

(List continued on next page.)

OTHER PUBLICATIONS

Article: Trock, David H. et al., "The Effect of Pulsed Electromagnetic Fields in the Treatment of Osteoarthritis of the Knee and Cervical Spine. Report of Randomized, Double Blind, Placebo Controlled Trials", pp. 1903–1911, The Journal of Rheumatology, 1994; 21–10.

(List continued on next page.)

Primary Examiner—Max F. Hindenburg
Assistant Examiner—Joseph A. Cadugan
(74) Attorney, Agent, or Firm—Volentine Francos, PLLC

(57) ABSTRACT

A method for stimulating growth in biological tissue or sprouts, an apparatus and a use thereof employs fluctuating magnetic fields. The apparatus includes a pulse generator and a plurality of coils in which pulsed currents will cause fluctuating magnetic fields in a predetermined region holding the material to be stimulated. The fluctuating magnetic fields will induce an electric field in the material. An enhanced effect has been detected in the regions where the electric fields are largest. The coils include a number of pairs of coils having, during a given pulse, magnetic fields in opposite directions in order to provide field gradients in the cells, micro organisms or tissue. Selecting a suitable number, size and positioning of coils will provide a homogeneous electric field in the predetermined region, which does not have any undesirable peaked maxima. When four or more coils are used, they can be combined in pairs arranged on opposite sides of the predetermined region, and with the adjacent coils conducting current in opposite directions and the opposing coils conducting currents in the same direction. Thereby, the induced electrical fields add constructively inside the regions between the pairs of coils. In an apparatus for stimulating cell proliferation and differentiation, it is a desired feature that the generated fluctuations in the magnetic fields do not elicit action potentials of living cells since this will cause great inconvenience for the patient.

49 Claims, 11 Drawing Sheets

U.S. PATENT DOCUMENTS

| | | | | | |
|---|---|---|---|---|---|
| 4,428,366 | A | * | 1/1984 | Findl et al. | 600/14 |
| 4,548,208 | A | * | 10/1985 | Niemi | 600/14 |
| 4,550,714 | A | * | 11/1985 | Talish et al. | 600/14 |
| 4,590,922 | A | * | 5/1986 | Gordon | 600/10 |
| 4,641,633 | A | * | 2/1987 | Delgado | 600/13 |
| 4,672,951 | A | * | 6/1987 | Welch | 600/14 |
| 4,785,575 | A | * | 11/1988 | Shioi | 47/1.3 |
| 4,994,015 | A | | 2/1991 | Cadwell | 600/13 |
| 5,010,897 | A | * | 4/1991 | Leveen | 600/13 X |
| 5,084,003 | A | * | 1/1992 | Susic | 600/13 |
| 5,156,587 | A | * | 10/1992 | Montone | 600/13 |
| 5,224,922 | A | * | 7/1993 | Kurtz | 600/13 |
| 5,314,400 | A | * | 5/1994 | Tsyb et al. | 600/9 |
| 5,344,384 | A | * | 9/1994 | Ostrow et al. | 600/13 X |
| 5,453,072 | A | * | 9/1995 | Anninos et al. | 600/9 |
| 5,480,373 | A | * | 1/1996 | Fischer et al. | 600/14 |
| 5,518,496 | A | | 5/1996 | McLeod et al. | 600/14 |
| 5,556,418 | A | * | 9/1996 | Pappas | 600/13 X |
| 5,718,662 | A | | 2/1998 | Jalinous | 600/13 |
| 5,738,625 | A | | 4/1998 | Gluck | 600/9 |
| 5,935,516 | A | * | 8/1999 | Baugh | 600/14 X |
| 5,997,464 | A | * | 12/1999 | Blackwell | 600/13 |
| 6,042,531 | A | * | 3/2000 | Holcomb | 600/13 |
| 6,123,658 | A | * | 9/2000 | Schweighofer et al. | 600/13 |
| 6,142,927 | A | * | 11/2000 | Clark | 600/9 |
| 6,200,259 | B1 | * | 3/2001 | March | 600/9 |

FOREIGN PATENT DOCUMENTS

| | | |
|---|---|---|
| EP | 0788813 A1 | 8/1997 |
| EP | 0 940 157 A2 | 9/1999 |
| WO | WO 85/00293 | 1/1985 |
| WO | WO 97/40887 | 11/1997 |
| WO | WO 99/10041 | 3/1999 |

OTHER PUBLICATIONS

Article: Patino, Osvaldo et al., "Pulsed Electromagnetic Fields in Experimental Cutaneous Wound Healing in Rats", pp. 528–531, Journal of Burn Care & Rehabiliation, vol. 17, No. 6, Part 1, Mar. 1996.

Article: Portier, Christopher, and Wolfe, Mary S. (editors), Assessment of Health Effects from Exposure to Power–Line Frequency Electric and Magnectic Fields, pp. 256–257, NIH Publication No. 98–3981, Aug. 1998.

Article: Bassett, C.A.L. et al., "A Non–Operative Salvage of Surgically–Resistant Pseudarthroses and Non–Unions by Pulsing Electromagnetic Fields", pp. 128–142, Clinical Orthopaedics and Related Research, No. 124, May 1977.

Article: Sisken, B.F. et al., "Stimulation of rat sciatic nerve regeneration with pulsed electromagnectic fields", pp309–316, Brain Research, 485, (1989).

Article: Bassett, C.A.L. et al., "Treatment of Ununited Tibial Diaphyseal Fractures with Pulsing Electromagnetic Fields", pp. 511–523, The Journal of Bone and Joint Surgery, vol. 63–A, No. 4, Apr. 1981.

* cited by examiner 1101  1102

METHOD AND AN APPARATUS FOR STIMULATING/ MODULATING BIOCHEMICAL PROCESSES USING PULSED ELECTROMAGNETIC FIELDS

CROSS-REFERENCE TO RELATED APPLICATIONS

The present application claims priority under 35 U.S.C. §119 to Danish Patent DK PA 1999 01207, filed Aug. 31, 1999 and U.S. Provisional Application Serial No. 60/157, 042 filed Oct. 1, 1999, the entire contents of both of which are hereby incorporated by reference in their entirety for all purposes.

FIELD OF THE INVENTION

The present invention provides a method and an apparatus for stimulating and/or modulating growth and differentiation in biological or plant tissue, seeds, plants, and microorganisms. An apparatus of this type includes a pulse generator and a plurality of coils, in which pulsed currents cause fluctuating magnetic fields in a predetermined region holding the material to be stimulated. The fluctuating magnetic fields will induce an electric field in the material.

BACKGROUND OF THE INVENTION

Pulsed electromagnetic fields (PEMF) have been used widely to treat delayed non-heating fractures, pseudoarthrosis, osteoarthritis, bone fractures and related problems (Bassett, C. A., Mitchell, S. N. & Gaston, S. R. (1981); (Trock et al., 1994). "Treatment of ununited tibial diaphyseal fractures with pulsing electromagnetic fields", *Journal of Bone and Joint Surgery* [*American*], 63-A, 511–523 and Bassett, C. A. L., Pilla, A. A. & Pawluk, R. J. (1977) "A non-operative salvage of surgically-resistant pseudarthroses and non-unions by pulsing electromagnetic fields: a preliminary report", *Clinical Orthopaedics*, 128–143) and have also been suggested for the treatment of nerve growth and wound healing (Sisken, B. F., Kanje, M., Lundborg, G., Herbst, E. & Kurtz, W. (1989), "Stimulation of rat sciatic nerve regeneration with pulsed electromagnetic fields", *Brain Research*, 485, 309–316 and Patino, O., Grana, D., Bolgiani, A., Prezzavento, G., Mino, J., Merlo, A. & Benaim, F. (1996), and "Pulsed electromagnetic fields in experimental cutaneous wound healing in rats" *Joural of Burn Care and Rehabilitation*, 17, 528–531). It has been suggested that some of the important effects relating to an enhanced bone growth is the PEMF-induced promotion of angiogenesis, but this issue is not yet resolved (The National Institute of Environmental Health Services (NIEHS): "Assessment of Health Effects from Exposure to Power-Line Frequency Electric and Magnetic Fields". (http://www.niehs.nih.gov/emfrapid/home.htm)).

A temporarily varying magnetic flux through an area induces an electric field, E, along the perimeter of the area according to the basic laws of electromagnetism. If the varying magnetic field, B(t), is applied to a material containing free (or mobile) charge carriers, these will be accelerated by the electric field thereby generating eddy currents in the material. The induced electric field or the generated current depends upon the rate of change, dB/dt, of the magnetic field, the electric field or current increasing with increasing rate of change.

The main point in treating biological tissue i.e. bone healing, wound healing, nerve growth, and angiogenesis is the introduction of tissue currents with an intensity and duration that can activate cellular signalling processes and extracellular signals, thus initiating cell proliferation and differentiation and other biological processes.

WO 85/00293 and WO 99/10041 describe the use of conducting coils to stimulate growth and healing in living tissue. The coils are positioned so as to generate a strong field at the region to be treated and a pulsating current signal is supplied for conduction in the coils.

PEMF has been used for activating muscle and neural cells as an alternative method to electrodes see e.g. EP 788 813 or U.S. Pat. No. 5,738,625. PEMF induced by conducting coils has the advantage that no electrodes in direct contact with the skin have to be used. The PEMF used for activating cells must be fast and/or large enough to induce electric potentials large enough to elicit the action potentials of excitable cells. In order to achieve such large electrical potentials, very large currents are used in the coil and the fields from several coils are added. In EP 788 813, the PEMF is used to activate muscle cells to flex a group of pelvic floor muscles in order to treat urinary incontinence. In U.S. Pat. No. 5,738,625, the PEMF is used to activate neural cells in order to investigate or diagnose the nervous system.

The effects of fluctuating magnetic fields in the tissue can be anticipated to be due to the effect of the induced electric field upon charged particles and entities (ions, molecules and macromolecules such as proteins, and inositol phosphates and other signalling compounds, cells and their extracellular signalling compounds such as hormones and other neurotransmitters etc.). Hence, the effects of fluctuating magnetic fields can be anticipated to be due to the extracellular as well as intracellular events caused by the electric fields and currents.

Regarding extracellular effects it can be expected that the on and off rate constants for the associations between neurotransmitters, hormones and their receptors will be affected, to the extent that net positive or negative charges are associated with the process, as well as inducing piezo-electric currents in bone tissue, thus mimicking physiological processes. The intracellular effects that might be the most affected are biochemical reactions that are involved in promoting cell division and differentiation. Amongst cellular signalling processes that have been suggested to be essential for the initiation of cell proliferation is the activation of protein kinase A. This enzyme is activated by cAMP (cyclic adenosine 5' monophophate) that is synthesised from ATP by a receptor activated adenylyl cyclase. cAMP binds to protein kinase A and forms catalytic subunits, and this signal can be carried to the nucleus. Here it leads to activation of cAMP-inducible genes. Activation of the synthesis of cGMP, by iron containing enzymes such as nitrogen oxide synthetase that in turn activates classes of protein kinase G, are also important candidates. Several studies have implicated that the activation of ornithine decarboxylase, causing synthesis of prutescine and other related compounds, that promotes DNA transcription, also appear to be essential. The mechanism by which signalling processes are initiated appear to be due to a combined effect of proteins with a net charge, that will move in the cell interior (G-proteins, protein kinases, mRNA binding proteins etc.). Those can associate with target proteins and exert a biological effect and changes in the association constants for these processes will affect cellular function. Other ions, such as $Ca^{2+}$, are highly affected by electrical fields, and will also exert a biological effect by associating with intracellular proteins and ion channels. The essential point is that signalling molecules with net charges or areas with net charges will be affected by the changing magnetic fields and all charged particles will rotate in magnetic fields depending on movements relative to the magnetic field.

One important aspect of promoting growth of osteoblasts, chondroblasts, chondrocytes and their derivatives (bone and cartilage), nerve cells, and other tissues is the induction of growth of small vessels (capillaries) that supply the blood cells, hormones and nutrients for sustaining cell proliferation and differentiation. The small vessels consist of endothelial cells, smooth muscle cells, and other cell types that together will protrude into new areas following the activation of nitric oxide (NO) and growth factors. These cells are also connected to each other both through signalling by chemical substances but also electrically through gap junctions. Both NO, vascular endothelial growth factor (VEGF) and other factors, appear to play an essential role in activating growth and differentiation amongst other things through activation of MAP kinase signalling pathways. However, the intracellular signalling processes play an equally important role in the cellular activation and when considering the effects of PEMF on angiogenesis both extracellular as well intracellular events should be considered.

The induced electric field from a circular coil can be calculated in a plane parallel to the coil, at a given distance from the coil. Due to the cylindrical symmetry, the induced electric field will have a circular symmetry in the plane, and have a maximum at a circle centered at the center axis of the coil with a radius, r, smaller than the radius, R, of the coil. As the distance from the coil to the plane increases, the peak of the maximum flattens out and the radius of the ring shaped maximum varies slightly. Thereby, the maximum of the induced electrical field in a direction away from the coil, form a tubular region centered on the center axis of the coil, and in a plane at a given distance from the coil, the induced electrical field will have a ring shaped maximum with a minimum in the center.

In the apparatuses of the prior art, the region to be treated is centered in the coil thereby experiencing an approximately homogeneous induced electrical field while the ring shaped maximum is positioned in regions encircling the region to be treated. Hence all-over, the field is inhomogeneous.

The biochemical features outlined in the above take place at a large range of electric fields. However, if the induced electrical field gets too high in the region to be treated, it will lead to elicitation of action potentials of excitable cells in the region. Elicitation of cellular action potentials is normally undesirable since it may lead to nuisance for the patient or give rise to undesirable physiological reactions. For example, the effects of the large induced electrical fields in EP 788 813 or U.S. Pat. No. 5,738,625 are a flexing of muscles due to activation of muscle cells or elicitation of nerve impulses due to activation of neural cells. These are undesirable side effects for a person undergoing a continuous treatment.

Therefore, under normal conditions it is not possible simply to increase the current or its rise time in the coils in order to achieve a larger induced electrical field over the region to be treated. The average field can only be increased until the field at the ring shaped maximum reaches the limit for elicitation of the action potentials of cells. Thus the average induced electrical field in the larger central part will not be increased to a very high degree. Hence by increasing the current or its rise time, the field in the region to be treated can only be brought to an average value lying considerably lower than the limit for elicitation of the action potentials of cells. In order to maintain the homogeneous field in the region to be treated, one will pay the price of a lower field and a large stimulation in the surrounding regions, which are not to be treated.

SUMMARY OF THE INVENTION

It is therefore an object of the present invention to provide a method and apparatus that stimulates biological tissues that substantially overcomes one or more of the problems due to the limitations and disadvantages of the related art.

The present invention utilizes the realization that stimulation of the biological tissue depends on the magnetic field in a way not previously anticipated. According to investigations performed by the inventors, there is an improved stimulation of the biological tissue in regions lying above or below the perimeter of the coil and not in the regions lying above the center of the coil. Also, the investigations showed that a continuous treatment for longer periods of time (few hours to several days) is often desirable. Hence the efficiency of the biochemical features outlined in the above and giving rise to treatment of biological tissue i.e. bone healing, wound healing, nerve growth and angiogenesis, depends on the induced electrical fields. In order to optimize the effects in the region to be treated, it is desirable to increase the induced electric field in this region and to have a constant average field over the region.

Especially, it has been found that larger B- and/or E-field gradients seem to have a positive effect on the cells, tissue and microorganisms. Such gradients may especially be formed by two coils oppositely polarized and positioned adjacently in relation to the cells. In this manner, especially in the intermediate area of the fields of the coils a larger field gradient is obtained. This effect has not been described hitherto.

The present technique imposes movement of ions and proteins in the tissue from all germinal layers that affects cellular activity in individual cells and in biological tissue as a whole. Important factors are the magnitude of the driving force (through imposing a changing magnetic field strength) with the direction of the magnetic field vectors; the frequency and shape of the pulses and the electrical potential. Those factors determine to which extent a compound possessing a net charge (ions, macromolecules etc.) are affected in a way such that a biological process (proliferation and differentiation) is initiated. The energy level by which the tissue is affected preferably does not cause significant changes in membrane potential and does not evoke action potentials in excitable tissues.

In a first aspect, the invention relates to an apparatus for stimulating living cells, micro organisms, and/or tissue using pulsed electromagnetic fields, the apparatus including a plurality of electrically conducting coils each having center axis, each center axis being directed into the cells, micro organisms, and/or tissue; and a pulse generator operationally connected to each coil for supplying a series of current pulses for conduction in each coil, the series of pulses being adapted to generate a periodically varying magnetic field from each coil for inducing an electrical field, wherein a number of coil pairs, including a first coil and a second coil adjacent to the first coil, exist in each of which, for a given pulse supplied by the pulse generator, the magnetic field at the center of the first coil is directed toward the cells, micro organisms, and/or tissue and the magnetic field at the center of the second coil is directed away from the cells, micro organisms, and/or tissue.

Thus, by providing pairs of coils where the desired E-field gradients are provided, a better influence on the tissue/cells/ micro organisms is provided. It should be noted that, naturally, a given coil could be part of a number of pairs in that it will normally have more than one adjacent coil in the apparatus.

In the present context, the center axis of a coil is a symmetry axis normally directed along the central axis of a tubular coil or perpendicularly (positioned centrally) to a plane of a flat coil.

In order to obtain the desired effect over an area exceeding that of merely two coils, it is normally preferred that the number of pairs exceeds half the number of coils in the plurality of coils such as that the number of pairs exceeds 3/4 times the number of coils in the plurality of coils, such as 0.8 times the number of the plurality of coils, such as 0.9 times the number of the plurality of coils, such as being at least substantially equal to the number coils in the plurality of coils. In fact, coil positioning structures exist in which the total number of such pairs exceeds the number of coils in the apparatus by more than a factor of two.

Another manner of defining this manner of obtaining the desired gradients is to provide the apparatus with coils so that, for the given pulse supplied by the pulse generator, in each pair of coils, the first coil is adapted to conduct the current pulse in a clockwise direction and the second coil is adapted to conduct the current pulse in a counter-clockwise direction taken along the center axes of the first and second coils, respectively, in a direction toward the cells, micro organisms and/or tissue.

Again, preferably the first coil of each pair is adapted to conduct the current pulse in a clockwise direction and wherein two, three or more of the nearest neighboring coils of the first cell are adapted to conduct the current pulse in a counter clock-wise direction taken along the center axes of the coils in a direction toward the cells, micro organisms and/or tissue.

Naturally, the number of coils will depend on the actual use of the apparatus—and on the size thereof.

A cross section of each coil, perpendicularly to the center axis, may be at the most 100 $cm^2$, such as at the most 50 $cm^2$, preferably at the most 25 $cm^2$, such as at the most 10 $cm^2$, such as at the most 9 $cm^2$, preferably at the most 8 $cm^2$, such as at the most 7 $cm^2$, preferably at the most 6 $cm^2$, such as at the most 5 $cm^2$, preferably at the most 4 $cm^2$, such as at the most 3 $cm^2$, preferably at the most 2 $cm^2$, such as at the most 1 $cm^2$, preferably at the most 0.5 $cm^2$, such as at the most 0.4 $cm^2$, preferably at the most 0.3 $cm^2$. Smaller coils make it possible to use a large number of coils whereas larger coils are able to provide larger fields—such as for use at a larger distance, such as for treating cells, tissue and/or micro organisms inside a container or body.

Normally, the apparatus would include more than 2 coils, and depending on a number of factors, the number of coils may exceed 2, 4, 6, 8, 10, 14, 18, 20, 24 or more.

Naturally, the shape of the coils may be any shape desired. The shape of the coils will be determined on the basis of ease of manufacture, availability and requirements as to the individual positioning.

By using a number of, especially smaller, coils, the induced electric field at a given depth will have many smaller ring shaped maximum regions instead of one large ring shaped maximum region—together with a number of the desired high gradient areas. Thereby the total induced electric field will be more homogeneous and have a higher average value without eliciting any cellular activation potentials. Also the ratio between low field regions within ring shaped maxima and the total region to be treated is reduced.

The current pulses conducted in the coils preferably include rising and declining phases (two, three or more) resulting in the imposition of an electric field on the charges in the region to be treated. The overall duration of these events may vary depending on the pulse pattern. Thus, the events include increasing and declining magnetic fields that cause the appearance of temporally dependent electric fields on charged particles in particular directions in the tissue. These fields gives rise to the currents in the cells and extracellular environment consisting of moving ions and macromolecules such as proteins and nucleotides as well as amino acid, inositol phosphates and other charged signalling molecules. Thereby, cells are activated in fashion different from events such as i.e. action potentials.

Normally, each coil has a part being at least substantially perpendicular to the center axis of the coil and being adapted to face the cells, micro organisms and/or tissue, the parts of the coils being positioned in one or more planes each including a plurality of coil parts.

The coil may be a flat coil where the part will then be a side surface thereof. Alternatively, the coil may be tubular, where the part would then normally be an end portion thereof.

In order to fit in as many coils in the space as possible, it may be preferred that the parts of the coils within a predetermined area in one of the one or more planes are positioned so as to form so-called closest packing. The closest packing being a manner of packing circular elements optimally.

Also, at least one of the coils may have a part within the predetermined area and has a center to center distance to a nearest neighbor being between 1D–1.5D, where D is the diameter of the one coil.

Different structures may be used in order to provide as many pairs as possible providing the desired gradients. In fact, one preferred structure is the above closest packing which, unfortunately, provides also adjacent coils providing fields in the same direction. Another interesting structure is a honeycomb structure where it is possible for all three coils adjacent to a given coil to have the opposite field than the given coil.

In one embodiment, the plurality of coils is embedded in a flat sheet of flexible material for at least partly surrounding the predetermined cells, microorganisms and/or tissue. Thus, a bendable sheet is provided for surrounding a container, a body part or the like.

In another embodiment, the apparatus includes an even number, larger than two, of coils arranged in sets of two, the coils of each set being adapted to be positioned on at least substantially opposite sides of the cells, micro organisms and/or tissue and having at least substantially coincident center axes. In this manner, the coils may be positioned in one or more flexible sheets or more rigidly fixed e.g. in a tong-like device for at least partly encircling the e.g. container or body part.

Each coil may have a ratio between its inductance and resistance resulting in a pulsed current with a rise time in the range from 0.1 ms to 2 ms and a maximum current corresponding to a maximum magnetic field of 0.05–0.1 Tesla at the center of the coil. This has been found suitable for enhancing angiogenesis in biological tissue.

Also, the pulse generator may be adapted to generate pulses with a frequency in the range from 1 to 300 Hz, such as 10–200 Hz, preferably 20–100 Hz.

Normally, the apparatus will include a power supply for supplying power to the pulse generator. Especially in order to provide a portable apparatus, the power supply may be a battery included within the apparatus and supplying an electric potential of 50 V or less.

Normally, the current pulses fed to the coils will be the same pulses. However, it is possible to actually provide different pulses to different coils, such as pulses having different frequencies. In that situation it is desired that those frequencies are multiples of a basic frequency so that the pulses may be provided at least substantially simultaneously.

It is preferred that the phases of the pulses have a temporal separation in order for the biochemical events to occur, and the two events are therefore normally separated by milliseconds. It has been found suitable to provide a delay of 0.01–10 ms, such as 0.05–5 ms, preferably 0.2–2 ms, such as on the order of 0.5 ms between adjacent pulses for the coils. Also, a time duration of 1–100 ms, such as 2–50 ms, preferably 5–20 ms, such as on the order of 10 ms of the pulses has been found preferred for some applications.

Also, it generally may be desired to provide a treatment over a prolonged period of time, such as a period of time exceeding 15 minutes, such as exceeding ½ hour, preferably exceeding 1 hour, such as exceeding 2 hours, such as exceeding 4 hours, preferably exceeding 10 hours, such as exceeding 15 hours, preferably exceeding 1 day, such as exceeding 2 days.

An especially preferred embodiment of the present apparatus is one being adapted to be carried by a person during an operation.

In that and other embodiments, it is desired that the apparatus further includes a fastener for fastening the coils to a body part of a human or animal.

The present invention also relates to two preferred devices that by use of conventional CMOS IC technology create the particular currents in the coils. The devices include timing circuits, made from standard CMOS IC's with low power consumption. They form a free running asymmetric square wave generator that for example produces an output pulse every 18 ms with a pulse with of for example 3 ms. This pulse is applied to the output stage. The pulse pattern can consist of one or two phases. A CMOS IC, that divides the pulse frequency by 100, drives a control lamp by counting the flashes. This makes it possible to make a simple evaluation of the generator functionality and its frequency. In addition in one device, a magnetometer is incorporated to check the battery and the coils for defects. This circuit includes a little sense coil, an amplifier, a peak rectifier and a comparator that, when beyond threshold, drives the control lamp to light permanently. The comparator threshold is passed when the stimulating coil is functioning correctly when held close to the location of the sense coil.

An alternative to the use of the sensing coil is to have the control lamp flash only when the coil current is within the limits that ensures correct functionality.

In another aspect, the invention relates to the use of the above apparatus. In this case in a second apparatus the coil current is sensed.

Especially, the invention relates to the use of the above apparatus for enhancing tissue growth in a human or an animal, the use including positioning the coils adjacently to the tissue in question and operating the pulse generator.

In this situation, the series of pulses and the coils are preferably selected so that the maximum regions of the induced electrical fields in the predetermined portion are sufficiently small in order not to elicit action potentials in living cells. Normally, a muscle cell or nerve is depolarized to an extent that the membrane potential from −90 mV (muscle) or −70 mV (nerve) reaches its threshold around −55 mV whereby an action potential is elicited. Thus, the present apparatus is able to treat the cells etc. without eliciting excitable tissues.

In one embodiment, the use includes positioning of the coils at the upper or lower jaw of the human or the animal for inducing an enhanced bone growth, such as after extraction of a tooth.

In another embodiment, the use includes positioning the coils at the upper or lower jaw of the human or the animal for promoting in-growth of dental implants.

In yet another embodiment, the use includes attaching the coils to a joint region of the human or the animal for treatment of arthritis or pain, and/or for promoting growth of bone and/or cartilage and/or blood vessels (angiogenesis).

In an alternative embodiment, the use includes attaching two or more coils to a joint region of the human or animal to prevent arthritis or pain or to promote bone growth after a bone fracture.

In another embodiment the apparatus can be used for enhancing the biochemical activity of neural tissue. Three or more coils can be attached to the head and transcranial stimulation conducted without eliciting action potentials but enhancing neural activity resulting in an increased neurosecretion and/or in cell division. This can be applied for i.e. the treatment of depression disorders.

Alternatively, the above apparatus may be used for treating microorganisms, the use including positioning the coils adjacently to the microorganisms in question and operating the pulse generator.

The above apparatus may also, as a matter of fact, be used for treating seeds, plants or plant tissue. This use will include positioning the coils adjacently to the seeds, plants or plant tissue in question and operating the pulse generator.

A third aspect of the invention is a method of treating micro organisms with pulsed electromagnetic fields, the method including providing the above apparatus, directing the center axes of the coils into the micro organisms, and operating the pulse generator.

A fourth aspect of the invention relates to a method for treating cells, micro organisms and/or tissue with pulsating electromagnetic fields, the method including providing a plurality of coils each having a center axis directed into the cells, micro organisms and/or tissue; and providing a series of current pulses to each coil, the series of pulses being adapted to generate a periodically varying magnetic field from each coil for inducing an electrical field, wherein for a given pulse of the series of pulses, and for a number of pairs of the coils, each pair including a first coil and a second, adjacent coil, the magnetic field at the center of the first coil is directed toward the cells, micro organisms, and/or tissue and the magnetic field at the center of the second coil is directed away from the cells, micro organisms, and/or tissue.

Again, it may be preferred that the number of pairs exceeds half the number of coils in the plurality of coils, such as that the number of pairs exceeds 3/4 times the number of coils in the plurality of coils, such as 0.8 times the number of the plurality of coils, such as 0.9 times the number of the plurality of coils, such as being at least substantially equal to the number of coils in the plurality of coils.

Also, it may be preferred to also have the step of providing a part of each coil, the part being at least substantially perpendicular to the center axis of the coil and being adapted to face the cells, micro organisms and/or tissue, in one or more planes each including a plurality of coil parts.

The parts of the coils may be provided within a predetermined area in one of the one or more planes are positioned so as to form the closest packing.

Also, at least one of the coils having a part within the predetermined area may be provided to have a center-to-center distance to a nearest neighbor being between 1D–1.5D, where D is the diameter of the one coil.

In one embodiment, the plurality of coils are embedded in a flat sheet of flexible material and at least partly surrounding the predetermined cells, micro organisms and/or tissue with the flat sheet.

In another embodiment, the providing step includes providing an even number, larger than two, of coils in sets of two, and positioning the coils of each set on at least substantially opposite sides of the cells, micro organisms and/or tissue so as to have at least substantially coincident center axes. Again, these coils may be provided within one or more flexible sheets or e.g. within a more rigid, such as a tong like, structure.

Normally, the method would further include providing a power supply for supplying power to the pulse generator. Especially for a portable apparatus or for safety reasons, the power supply may be a battery included within the apparatus and supplying an electric potential of 50 V or less.

Depending on the actual purpose of the method, the coils and the pulse generator may be desired to provide a series of pulses forming a temporal overlap between the varying magnetic fields from individual coils to form a periodically varying total magnetic field having a frequency in the range from 1 to 1000 Hz.

For the given pulse supplied by the pulse generator, in each pair of coils, the first coil may conduct the current pulse in a clockwise direction and the second coil may conduct the current pulse in a counter-clockwise direction taken along the center axes of the first and second coils, respectively, in a direction toward the cells, micro organisms and/or tissue.

Preferably, the first coil of each pair conducts the current pulse in a clockwise direction and two, three or more of the nearest neighboring coils of the first coil conduct the current pulse in a counter clock-wise direction taken along the center axes of the coils in a direction toward the cells, micro organisms and/or tissue.

Depending on the actual use, each coil may receive, in the series of pulses, a pulsed current with a rise time in the range from 0.1 ms to 2 ms and a maximum current adapted to provide a magnetic field of 0.01 Tesla at the center of the coil, and the pulse generator may generate pulses with a frequency in the range from 1 to 300 Hz.

In a number of applications, it is desired to have a number of coils, such as more than 2 coils, and depending on a number of factors, the number of coils may exceed 2, 4, 6, 8, 10, 14, 18, 20, 24 or more. In the same situation, it may be desired to then choose coils with smaller sizes than those normally used today. Therefore, the step of providing the coils preferably includes providing coils having a cross section, perpendicularly to the center axis, that is at the most 100 $cm^2$, such as at the most 50 $cm^2$, preferably at the most 25 $cm^2$, such as at the most 10 $cm^2$, such as at the most 9 $cm^2$, preferably at the most 8 $cm^2$, such as at the most 7 $cm^2$, preferably at the most 6 $cm^2$, such as at the most 5 $cm^2$, preferably at the most 4 $cm^2$, such as at the most 3 $cm^2$, preferably at the most 2 $cm^2$, such as at the most 1 $cm^2$, preferably at the most 0.5 $cm^2$, such as at the most 0.4 $cm^2$, preferably at the most 0.3 $cm^2$.

One interesting embodiment of the present aspect is the use thereof for treating human cells or tissue. Then, the method may include actually fastening the coils to a body part of a human or an animal. Alternatively, the coils may be provided fixed to e.g. a building, a wall or a bed or as a separate part, such as part of a mattress or a blanket.

Normally, the method includes positioning the coils adjacently to the cells, microorganisms and/or tissue in question and operating the pulse generator.

Preferably, especially when treating cells or tissue of living beings, the series of pulses and the coils are adjusted so as for the maximum regions of the induced electrical fields in the predetermined portion to be sufficiently small in order not to elicit action potentials in living cells.

In one embodiment, the method includes positioning the coils at an upper or lower jaw of a human or an animal for inducing an enhanced bone growth, such as after extraction of a tooth.

In another embodiment, the method includes positioning the coils at an upper or lower jaw of a human or an animal for promoting in-growth of dental implants.

The method may also include attaching the coils to a joint region of a human or an animal for treatment of arthritis or pain, and/or for promoting growth of bone and/or cartilage and/or blood vessels—so-called angiogenesis.

In a further embodiment, the method may include attaching two or more coils to a joint region of a human or an animal to prevent arthritis or pain or to promote bone growth after a bone fracture.

The method may also be performed for treating microorganisms. Then the method may include positioning the coils adjacently to the microorganisms in question and operating the pulse generator.

Alternatively, the method may be used for treating seeds, plants or plant tissue. Then the method may include positioning the coils adjacently to the seeds, plants or plant tissue in question and operating the pulse generator.

Finally, the invention also relates to a method of treating seeds, plants or plant tissue with pulsed electromagnetic fields, the method including providing an apparatus as described in relation to the first aspect, directing the center axes of the coils into the seeds, plants or plant tissue and operating the pulse generator.

These and other objects of the present invention will become more readily apparent from the detailed description given hereinafter. However, it should be understood that the detailed description and specific examples, while indicating the preferred embodiments of the invention, are given by way of illustration only, since various changes and modifications within the spirit and scope of the invention will become apparent to those skilled in the art from this detailed description.

BRIEF DESCRIPTION OF THE DRAWINGS

Preferred embodiments of the invention will now be described with reference to the drawings wherein.

DETAILED DESCRIPTION OF THE PREFERRED EMBODIMENTS

Figure 1A:
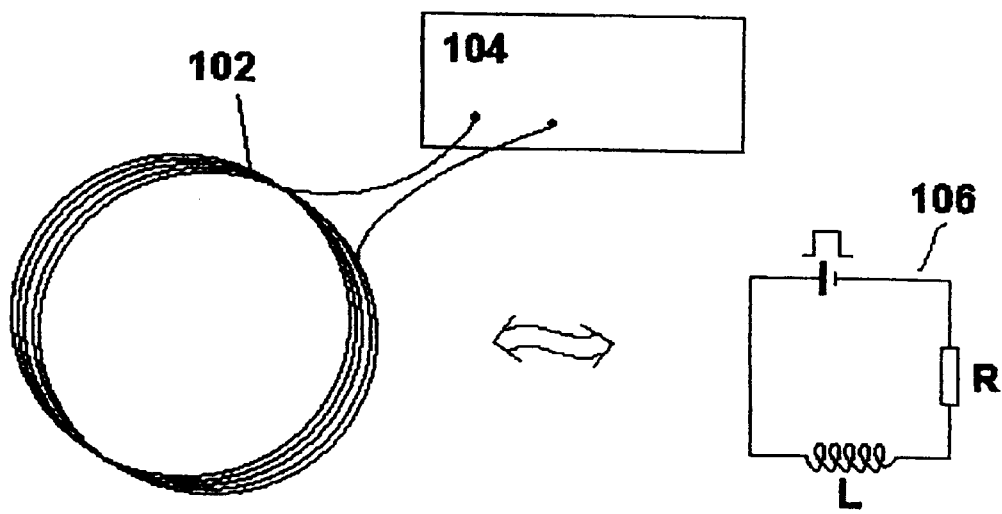
FIG. 1A is a schematic comparison of a prior art system and an electronic diagram thereof.
Figure 1B:
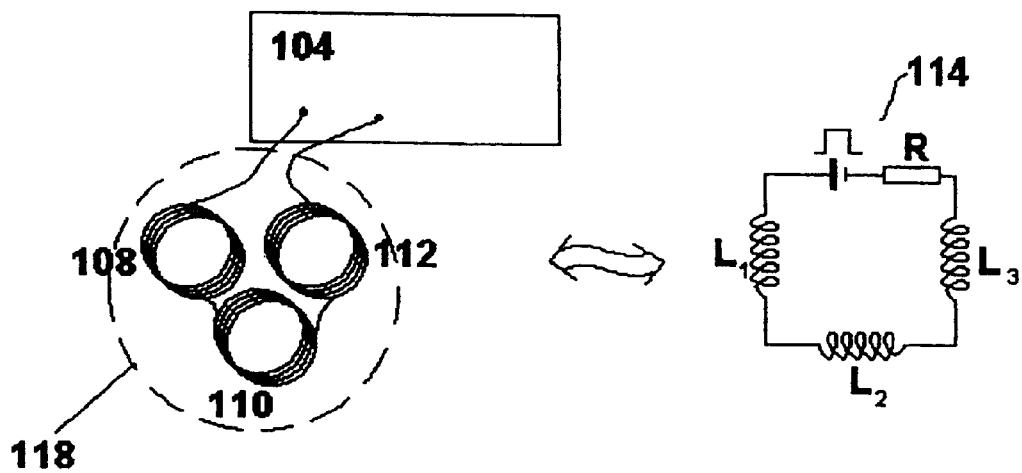
FIG. 1B is an illustration of an apparatus according to the invention and electronic diagrams of embodiments thereof.

FIGS. 1A and 1B illustrate a comparison between a related art apparatus and an apparatus according to the invention. The related art apparatus of FIG. 1A has a coil (102), having a given number of windings, and a current source 104. A schematic drawing (106) reveals its electrical properties with a current source, a resistance and an inductance.

The apparatus according to the invention shown in FIG. 1B includes three coils (108, 110 and 112) imbedded in a supporting frame (118) and connected to a current source (104). The electronic circuit (114) reveals the coil characteristics. The coils can be connected in series (114) and parallel (116).

Figure 2:
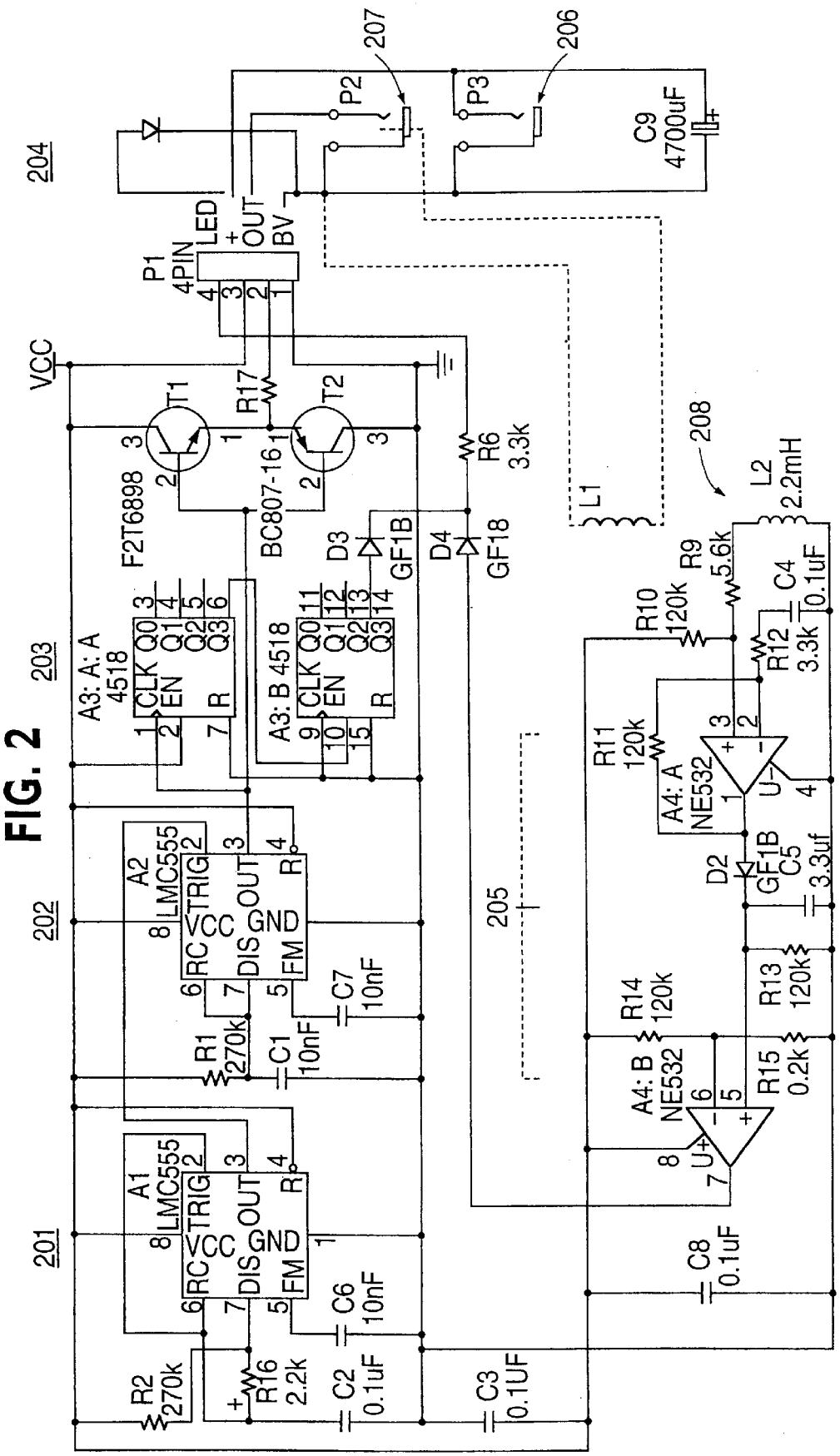
FIG. 2 is a circuit diagram for a preferred pulse generator for use in the apparatus according to FIG. 1B.

Pulse Generator (FIG. 2)

FIG. 2 is an illustration of a preferred circuit for providing current pulses with one phase for the coils and with a sense coil system that detects when magnetic fields are created by the connected coils. This circuit is composed of a 55 Hz oscillator (201), a one-shot 3 ms circuit (202), a divider (203) that provides division of 1/100 for a lamp, a front panel (204) providing output for coils (207) and external DC power (206), a magnetic field sense device (205) with a comparator on the left, a peak rectifier in the middle, and an amplifier at the right location. The circuit for the sense coil system is denoted (208).

Figure 7:
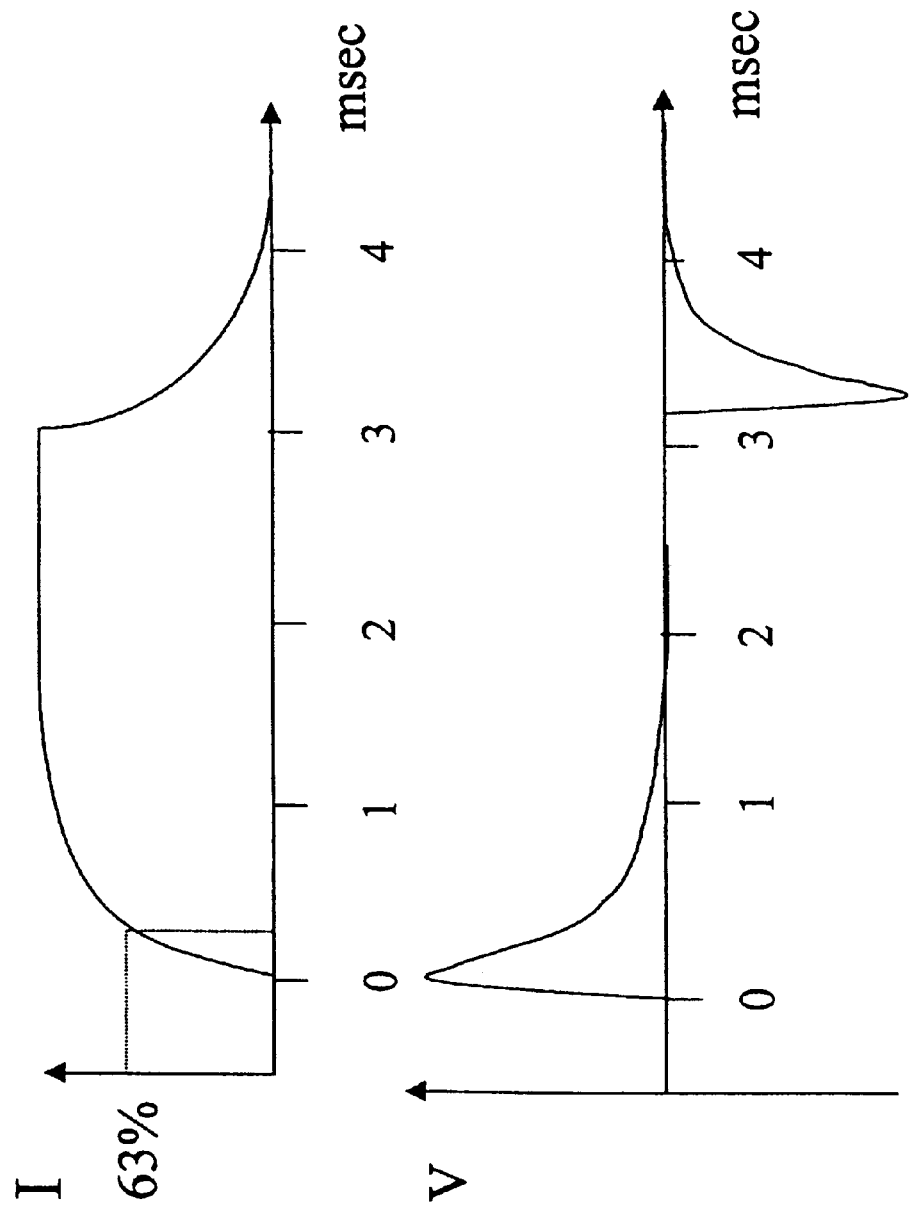
FIG. 7 illustrates the increase in voltage of a sensing coil positioned adjacently to a single coil, the upper curve illustrates the current in the sensing coil as a function of time and the lower curve illustrates the electromotive force imposed on charged particles as a function of time.

FIG. 7 illustrates measurements performed adjacently to a single coil. Illustrated is the increase in voltage in a sense coil placed underneath a single coil of the type used in this device. The rise in voltage was measured during pulse generations by an oscilloscope.

The upper curve illustrates the current in the coil as a function of time. The rise time for the current flow is a function of the inductance (L) and the resistance (R) of the coil circuit. As described elsewhere, the magnitude of L/R (63% of maximum current) is essential for the characteristics (duration and magnitude) of the electromotive force induced on charged particles in the tissue.

The lower figure illustrates the electromotoric force (V) imposed on charged particles (or electrons in a wire) as a function of time. The shape of this V/ms relationship is determined by the magnitude of the slope of the A/ms relationship in the upper curve.

The necessary power for the coils is either delivered by a handheld, battery operated pulse generator (FIG. 2) or from a power source yielding up to 50 V and the sufficient amount of current. The device includes electronic circuits, output switch, coil connector and a control lamp. The necessary power for stimulating the coils can be delivered by a handheld, battery operated pulse generator as shown in FIG. 2 (or alternatively a power supply providing up to 50V DC). The device uses conventional CMOS IC technology to create the particular currents in the coils. The device includes a timing circuit, made from standard CMOS IC's with low power consumption. It forms a free running asymmetric square wave generator that produces an output pulse i.e. every 18 ms with a pulse width of i.e. 3 ms. Those characteristics can be varied, and usually the desired frequency for pulse generation is between 1–100 Hz. The duration of the pulse will then change accordingly. This pulse is applied to the output stage, which includes two complementary emitter followers that supply the necessary output current and is able to withstand the transients from the current switching in the coil. An output switch can be made so that it selects different resistors placed in series with the coil in order to vary the output current. A CMOS IC, that divides the pulse frequency width by 100, drives a control lamp by counting the flashes. This makes it possible to make a simple evaluation of the generator functionality and its frequency. In addition, a magnetometer is incorporated to check the battery and the coils for defects. This circuit is formed by a little sense coil, an amplifier, a peak rectifier and a comparator that, when beyond threshold, drives the control lamp to be permanently on. The comparator threshold is exceeded when the stimulating coil is functioning correctly and is held close to the location of the sense coil.

Figure 8:
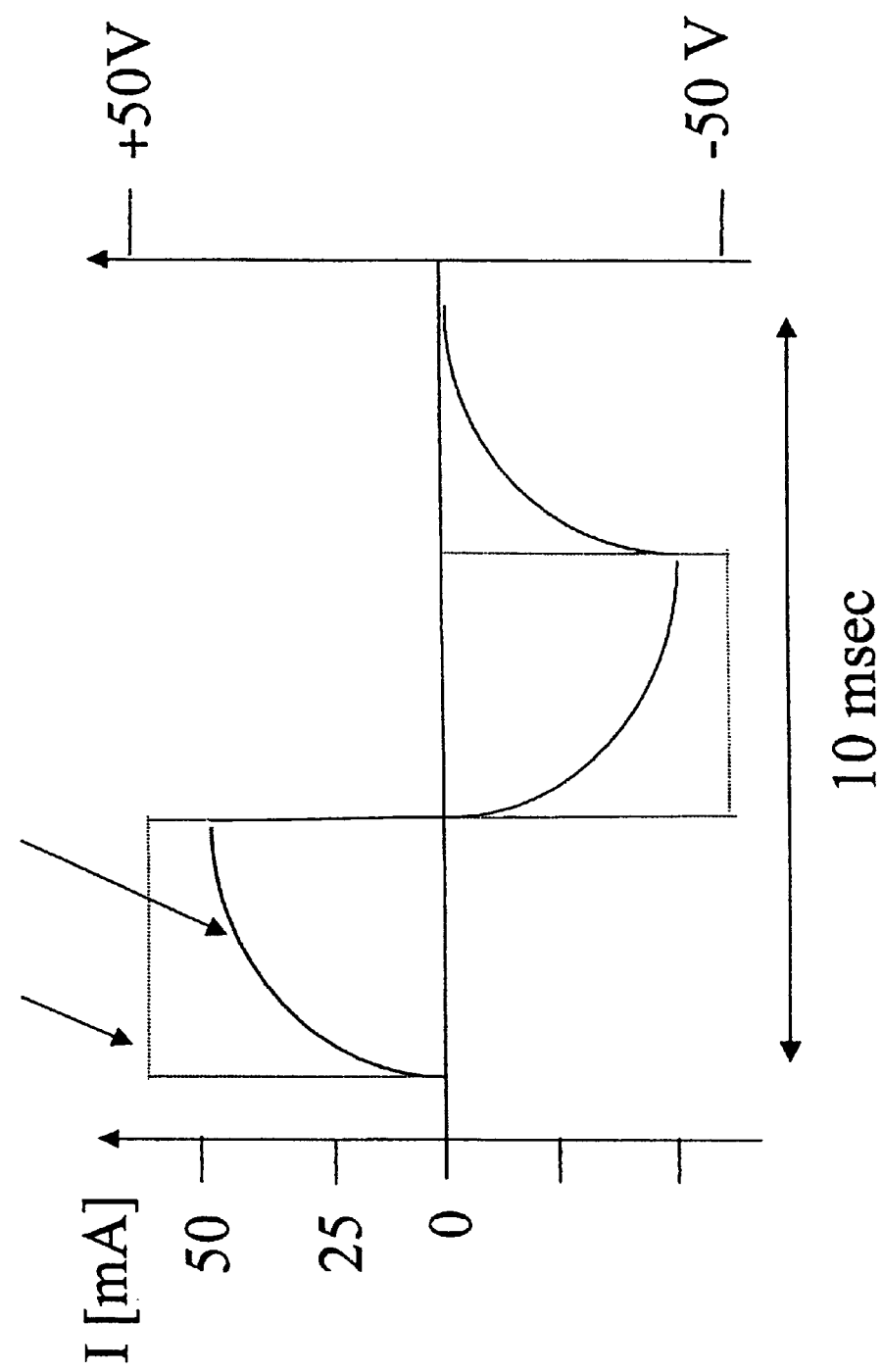
FIG. 8 illustrates an example of a series of pulses in which +50 V is imposed for 3 ms then followed by −50 V for 3 ms. This results in a rapid change in the current in the coils that causes a rapidly changing magnetic field.

The device can also include a larger cabinet, electronic circuits, power lead and power switch, coil connector and control lamp. Also, a device may use conventional CMOS technology to create the voltage needed for the particular currents in the stimulating coils. The electronic circuit includes a timing circuit that generates free running bipolar square pulse pairs. They can be produced (as in FIG. 8) every 18 ms with a duration of each pulse of 3 ms. These pulse pairs are applied to the output stage, which includes two complementary emitter followers that supply the necessary output current and is able to withstand the transients from the current switching in the coil. By measuring the output current, a control circuit checks the stimulating coils and their connection leads. A control lamp indicates correct function by blinking with 1.8 s intervals. FIG. 8 shows an example of a series of pulses in which +50 V is imposed for 3 ms then followed by −50 V for 3 ms. This results in a rapid change in the current in the coils that causes a rapidly changing magnetic field.

FIG. 8 illustrates voltage applied to the coils from a pulse generator giving + and −50 V. The increase in voltage (801) + or −50 V drives the current (802) in the coils that consist of three phases. In the first phase +50 V is applied, causing an increase in current with a rate constant determined by the L/R ratio. After 3 ms, −50 V is introduced and the current is reversed. This event lasts 3 ms, where after +50 V is introduced again. After approximately 10 ms the current is zero. The magnitude of the magnetic field is proportional to the current flow. The magnitude of the electromotoric force (EMF) on charged particles in the cells is proportional to the rate by which the current changes.

The full procedure in FIG. 8 lasts about 10 ms. It is highly desired that the events have a given duration in order for the biochemical events to occur. The 10 ms event can, however, be shortened up to five times by reducing the individual current transients. Thereby, the duration of the event can be as short as 2 ms. The frequency applied for sending pulses (composed of individual transients) can then i.e. vary between 2 and 500 Hz.

Construction of Coils

Figure 1B:
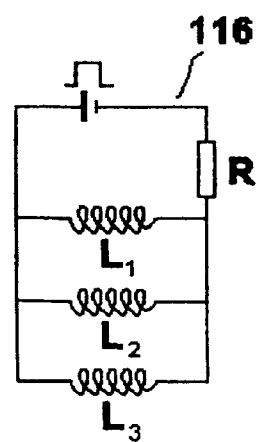

The basic principles for the construction of coils are shown in FIG. 1 with the pulse generator, the resistance and inductance. When constructing coils, it is important to introduce a large potential change of at least 0.1–10 ms duration in the tissue due to the relative slow on and off rate constants for interactions in biochemical signalling. The induced electric field can be estimated by considering the electromotoric force EMF introduced into a hypothetical circuit in the tissue:

$$EMF = -\frac{1}{c}\frac{d\Phi}{dt} = -\frac{1}{c}\frac{d}{dt}\int_S \vec{B}\cdot d\vec{S},$$

Where B is the strength of the magnetic field and Φ is the flux of the magnetic field through the area S. Hence the induced electric field is proportional to the current flow in the coil, whereby t is the time and c is the speed of light.

However, there is a limit as to how rapid a rise in the voltage, and consequently the current, which causes B to rise, can be increased in the coil. This is due to the fact that the coil possesses an induction (L) as well as a resistance (R). L will limit the rate by which the current can be applied since, as the current increases, an electromotoric force of opposite direction will occur originating in the coil material.

The inductance is equal to:

$$L = 4\pi k_m k'(n)^2 A l$$

Where L is the self-inductance in Henry (V s/A), $k_m$ is a constant equal to $10^{-7}$ (Tesla m/A), n is the number of windings, A is the area, and l is the length (m) of the coil.

The instantaneous electromotoric force induced is:

$$V = -L\, dI/dt$$

where I is the current (amperes) and t is the time (s).

Another important factor to consider for inducing rapid current changes in coils is to evaluate the ratio of the inductance over the resistance in the coil.

The rate of rise of current can be evaluated by integrating the equation (Ohm's law):

$$V_1 - V_2 - L(dI/dt) = RI$$

Resulting in:

$$I = (V_1 - V_2)/R(1 - e^{-Rt/L})$$

The time it takes the current to rise is thus proportional to τ=L/R, where τ (measured in s) is the time it takes to reach 63% of maximal current. Thus, if L becomes small, relative to a given R, by using fewer windings, τ becomes larger and the induced field, EMF=1/c dB/dt, larger. The insertion of iron in the center of the coil will also affect L (increase L) but the field lines will be more centered under and above the coil. Thus, coils should be constructed in such a way that L and R are matched to give the correct ratio, causing tissue currents of a sufficient magnitude and duration.

When the current is interrupted, an equally important event occurs resulting in a rapid decline in the magnetic field thus giving rise to new currents in the tissue in opposite directions. The coil material will now resist the new change in current flow and Ohm's first law gives:

$$-L(dI/dt) = RI$$

or by integration:

$$I = I_{max} e^{-(R/L)t}$$

Where $I_{max}$ is the original current flow before interruption, and the other symbols have their usual meaning. Thus, the current flow will stop with the time constant L/R. This factor thus determines the magnitude of current flow in the tissue when the pulse is interrupted. Surprisingly, if R is small, the duration of the current is longer. Since dB/dt thereby becomes smaller, the introduced current peak in the tissue will also be reduced. It is thus important to note the characteristics that create the waveforms that provide the driving force for ions and particles. In this embodiment, the coil positions have been uniquely matched, and the characteristics of the coils constructed in such a way that they together give the maximal effect in the tissue in the appropriate proximity.

The clinically applied pulsed electromagnetic fields normally have peak flux densities in the range of 0.1–5 mT (1–50 Gauss) with rise times in the order of hundreds of microseconds. This results in a typical dB/dt in the range of 1–50 T/s and corresponding peak induced electric fields of 0.1–1 V/m.

Coils

The preferred coils for treatment of i.e. osteoarthritis of the knee have a diameter of 5 cm, and a length of 2 cm. They contain 2800 windings with 0.2 mm Cu-wire and can thus be fitted to the side of the joint providing a frame for the adjacent coil technique. They have an inductance of 210 mHenry. The serial resistance of 140 (coil)+100 Ohm (circuit)=240 Ohm. For example L/R can be: L/R=0.210/240=875 $10^{-6}$ s. The device has been constructed in such a way that L/R can vary between 0.3 and 0.9 ms. Opposite those coils are two other coils of the same construction and with currents running in parallel with the opposite coil. Using for example 50 mA for each coil we obtain 45 Gauss in the center or 4.5 mTesla (measured with a Gauss meter). A rise time of half maximal magnetic force in 380 μs yields a dB/dt of 10 Tesla/s (in 0.38 ms). The induced electromotoric force in the tissue will then theoretically amount to 0.025 volts. This number will be reduced to 33% about 2 cm away from the coil surface (see FIG. 4). Thus, the rate of increase in the magnetic field will be around 3.3 Tesla/s. Introducing iron in the center of the coils will enhance the magnetic field, an effect that has been implemented in the coil construction.

A different set of coils have been constructed for treatment of bone growth in the jaws for patients that have been exposed for radiation therapy, for inserting implants or for promoting bone growth before the insertion of implants. Those coils have 2200 windings of 0.15 mm Cu-wire, have a width of 2.5 cm and are 1 cm long. With a current of 50 mA they yield 20 Gauss in the center. At a distance of 2 cm from the center they yield 6.6 Gauss. Those coils are placed as two adjacent coils on the surface of the skin. The coils can be constructed and inserted in soft material in such a way that they can be strapped to the tissue for different types of treatment (enhancement of bone growth and angiogenesis, acceleration of in-growth of dental implants).

Principle for the Adjacent Coil Technique
Two Coils

Figure 3:
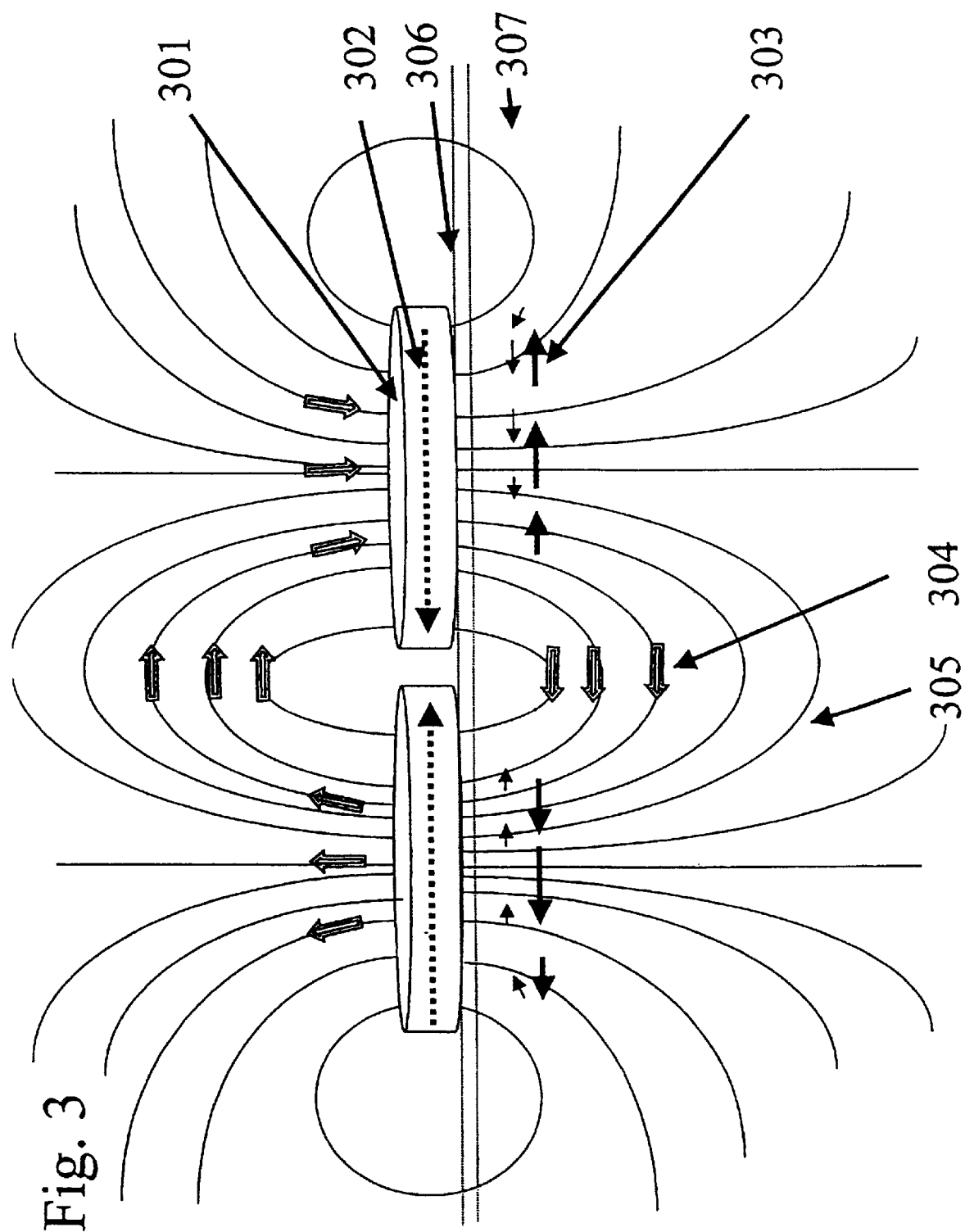
FIG. 3 illustrates the magnetic field lines originating from two coils positioned adjacently with oppositely directed magnetic fields.

The principle for the adjacent coil technique is shown in FIG. 3. This figure illustrates the magnetic field lines originating from the current pulses in a system consisting of two coils. A coil (301) has a current in given direction (302) creating magnetic fields revealed as magnetic field lines (305) with a given magnetic field vector (304). When the current in two coils is in opposite directions as in this figure the field vectors are added together since they have the same directions in the intersection between coils. The filled arrows 304 depict the intense currents that appear in biological tissue in the periphery and under the adjacent coil. In FIG. 3, the surface of the skin of the subject, e.g. a person, is denoted (306) and the underlying tissue (307).

Figure 4A:
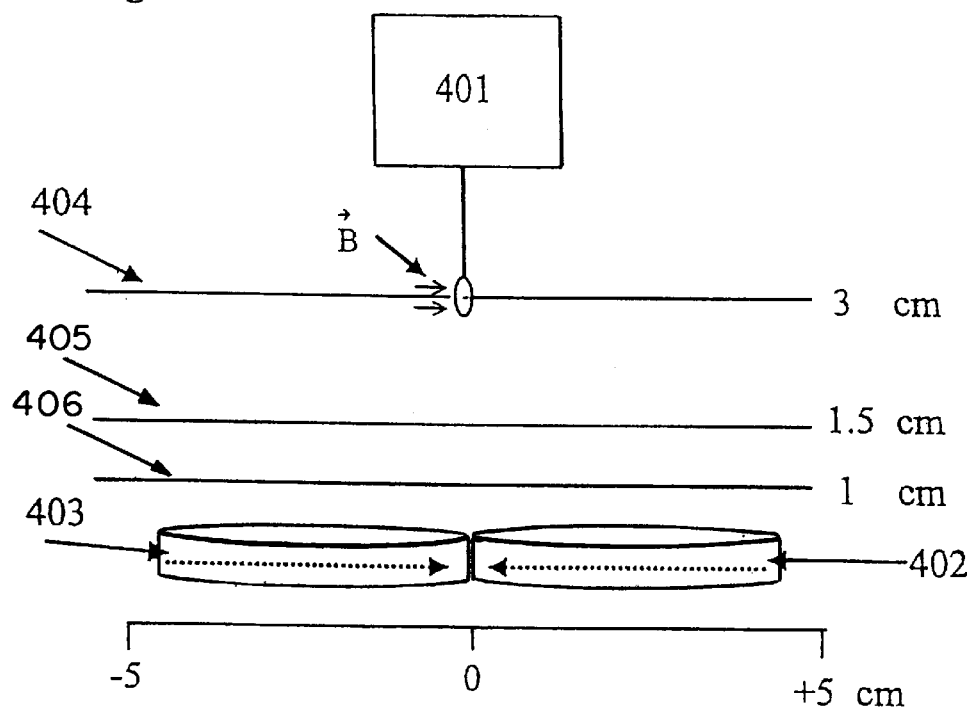
FIG. 4A illustrates a measurement of magnetic field intensities.

In FIG. 4A, measurements of magnetic field intensities (numerical values) along the three lines are depicted. A Gauss meter (401) (F. W. Bell, Gauss/Tesla Meter model 4048, Transverse probe model T- 4048-001 with the meter in the AC mode) was used to measure field vectors that are parallel to a line connecting the coil centers. Measurements were conducted along the lines (404, 405 and 406) that are positioned at a distance from the coils depicted in the figure.

Figure 4B:
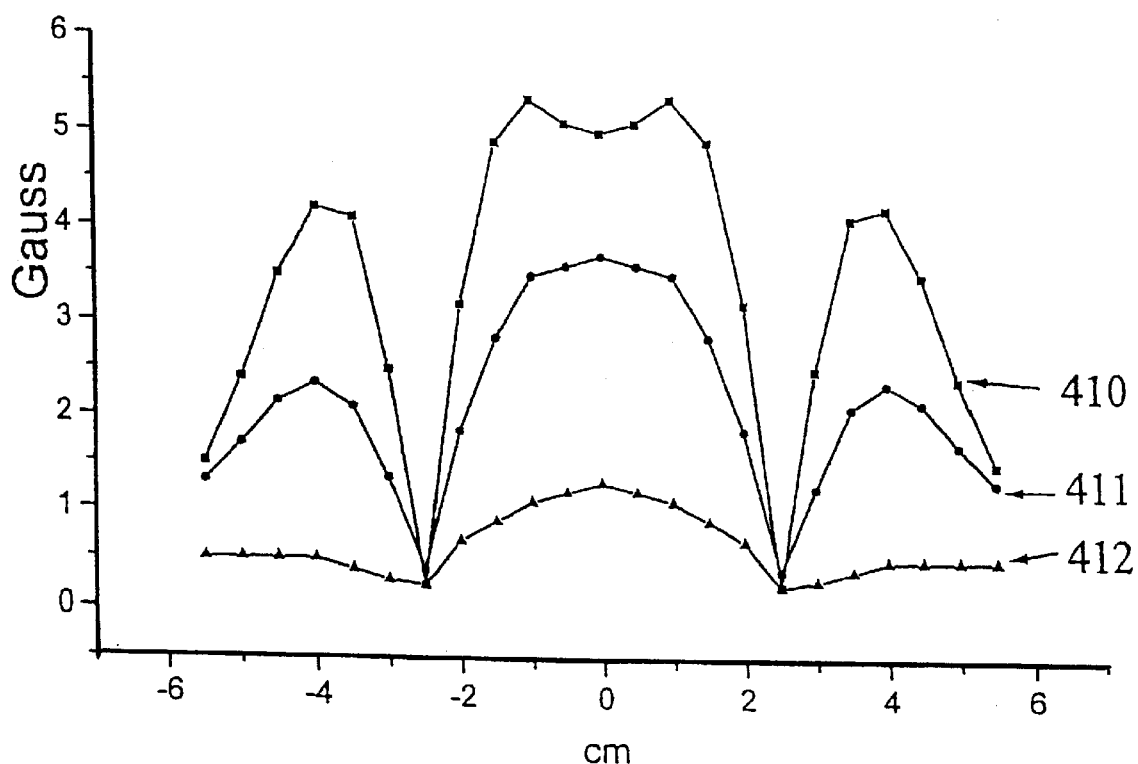
FIG. 4B illustrates the magnetic field lines originating from the current pulses in a system including two coils as illustrated in FIG. 3.

FIG. 4B illustrates magnetic field intensities (numerical values) from the three measurements at a constant distance from the coil surface that is either 1 cm (410); 1.5 cm (411); and 3 cm (412).

This figure illustrates the magnetic field lines originating from the current pulses in a system consisting of two coils. A coil (301) has a current in given direction (302) creating magnetic fields revealed as magnetic field lines (305) with a given magnetic field vector (304). When current in two coils are ine directions in the intersection between coils. The filled arrows 304 depict the intense currents that appear in biological tissue in the periphery and under the adjacent coils, whereby the surface of the skin is denoted as 306 and the tissue as 307. Note that at + and −2.5 cm from coil intersection, the field vector changes its numerical value. The coils were receiving current pulses of 75 mA and a duration of 3 ms with a rise time of 0.3 ms (63% of maximum).

With a magnetic field sensor placed perpendicular to the field vectors described above, we conducted measurements over the entire length of the two coils 1, 1.5 and 3 cm above the coils (FIG. 4B: 410,411 and 412). In the intersection area, where the coils meet, the magnetic field has its maximum value for the vector parallel to the coil axes. Above the center of the coils, the vector attains the value 0 (as expected from the drawing FIG. 3). In the periphery (away from the intersection) the magnetic field strength rises again and has an opposite sign, (but in FIG. 4B numerical values are used). When looking at the individual coils, the magnetic field lines have the highest density below and above the coil center. The magnetic field vectors from both coils (with currents in opposite directions), are added in the intersection and therefore in this location cause relatively large magnetic fields. This can be observed when the field lines are measured parallel to the coils as shown in FIG. 4B where it is evident that a large gradient appears in the tissue underneath the coils. When a third coil is added, two of the coils will have currents in the same direction and in this case a strong gradient appears at the intersections between these coils. All together when three coils are added a smaller or larger magnetic field gradient appears at different distances from the coils. This gradient provides the basis for the treatment of biological tissue. One large coil covering the same area would not provide the same size of the gradient and would therefore not be beneficial to the extent described for this invention.

Four Coils

Figure 5:
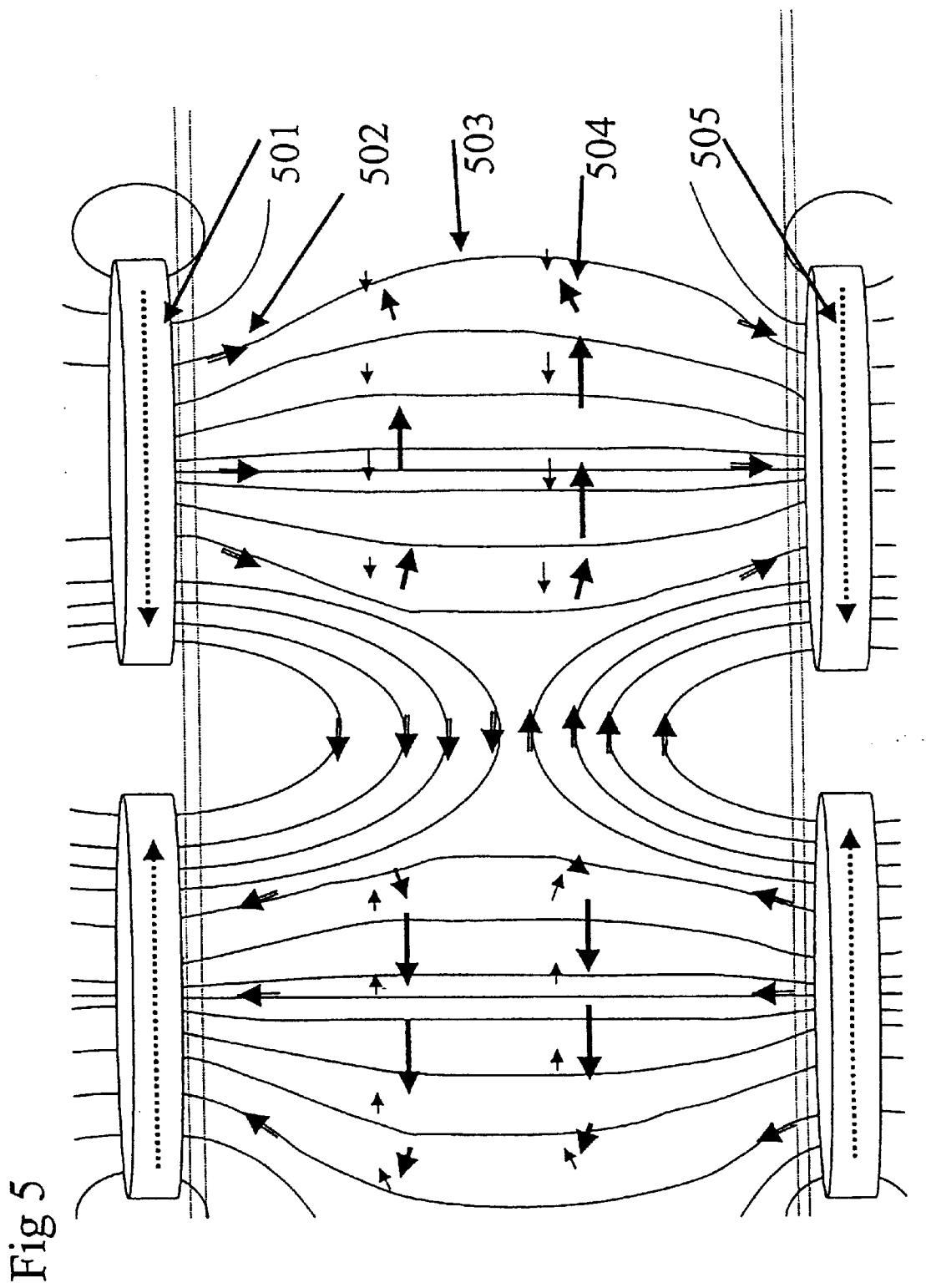
FIG. 5 illustrates magnetic field vectors in a situation were four coils are applied as two opposite sets.

FIG. 5 illustrates magnetic field vectors in a situation were four coils are applied. Four identical coils (501) are used with currents in a given direction (505). Note that both pairs of adjacent coils have currents oriented oppositely (as in FIG. 3). The coils that are placed across from each other have currents running in the same direction. Magnetic fields (503) have vectors (502) that are added in the intersection as in FIG. 4A. In FIG. 5, another gradient appears in the center between the four coils due to the oppositely directed vectors. The filled arrows (504) show the direction of the currents in the tissue.

Magnetic field strength was measured in the space between four coils in which each pair had current in opposite directions and opposite coils had currents in the same directions (FIG. 5). Thereby, enhanced field lines will be generated with a larger field gradient that was measured with the magnetic probe. The field line intensity was measured in the intersection between coils with the probe perpendicular to the field lines (605) measuring vectors parallel to the coil surface. In addition, line vectors perpendicular to the coils were measured at a line 2 cm from the coil center (604). The distance was set to 10 cm, that is, the distance usually required to i.e. treatment of joints with four coils. Alternatively, this distance can be set to a smaller value giving the same type of data but being applicable for treating elbows or other small joints. Larger distances can be used for treating hips or other, larger joints.

Figure 6A:
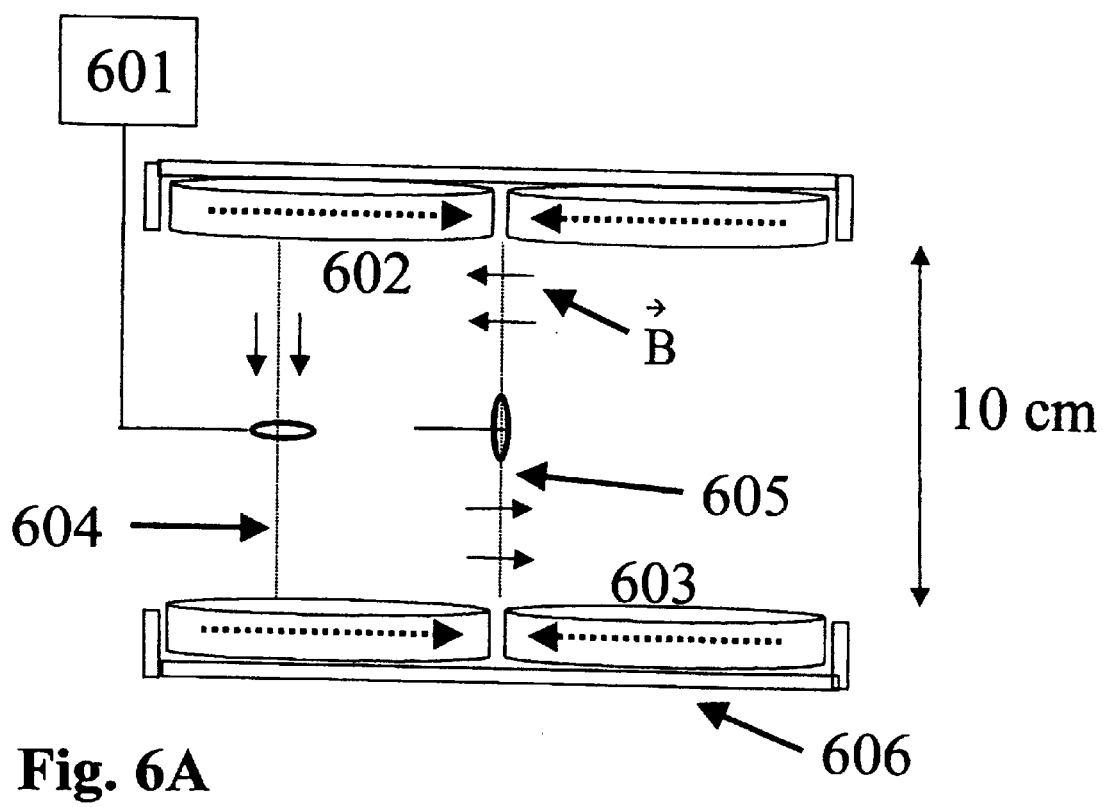
FIG. 6A illustrates a measuring of magnetic field intensities from the set-up of FIG. 5.

In relation to FIG. 6A, magnetic field intensities were measured originating from four coils with currents in the same direction (602,603) as illustrated also in FIG. 5. The intensities were measured by a Gauss meter with a sense coil (601) as described in FIG. 4A. Field vectors were measured along the line (604) with the coil oriented in such a way that field vectors perpendicular to the coil surface were determined. In the intersection between the four coils, the vectors parallel to the coils surface was determined along the line (605). In this figure, 606 indicates a supporting device used for strapping the coils to the surface such as i.e. the knee or elbow.

Figure 6B:
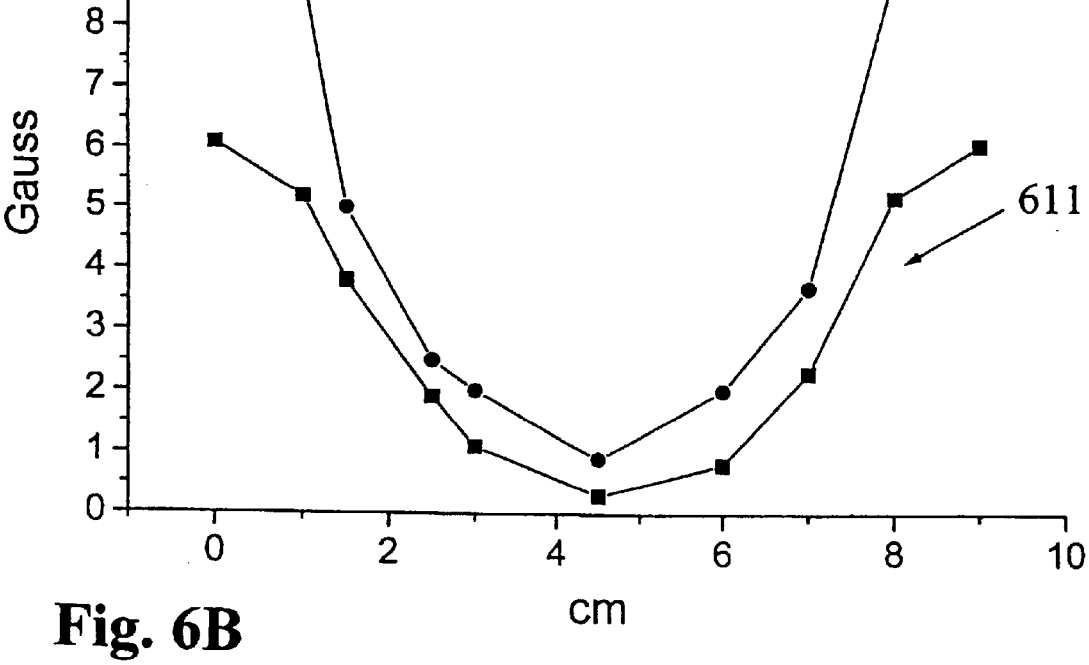
FIG. 6B represents the measurements from the measurement of FIG. 6A

FIG. 6B illustrates measurements of magnetic field intensities as described in FIG. 6A. The line (604) with vectors perpendicular to the coil surface gave intensities as shown (610) and the line 605 gave field intensities depicted as 611. Each coil received 38 mA current pulses with characteristics as in relation to FIG. 4B. FIG. 6B depicts the distance dependency. A strong magnetic field gradient appears also in the center between the four coils (611) revealing the beneficial effect of this use of four coils with larger gradients. Alternatively, more than two coils can be used adjacent each other—i.e. 3, 4 or more. Opposite those coils could also typically be positioned coils with currents in given directions providing basis for large field gradients.

These described characteristics of line field vectors between adjacent coils are only relevant for the vectors parallel to a line combining the axes of neighboring coils. It should, however, be emphasized that the total field strength, is a consequence of both this vector and the vector perpendicular to it describing the total field strength (B) using the equation:

$$B=\sqrt{(x^2+y^2)},$$

where x and y are the two types of line field vectors described above.

Description of Preferred Applications
Use of Coils for Treatment of Biological Tissue The coil characteristics according to the invention give a new perspective to treatment with pulsed electromagnetic fields. Relatively large changes in magnetic fields can be obtained with 9–50 V using the described technology and consequently large tissue currents can be introduced with resulting beneficial biological effects (bone heeling, wound heeling, cartilage regeneration, bone growth into implants, and other types of treatments). Thus, coils can be used for a variety of treatments, some of which are now approved by the Food and Drug Administration (FDA) in the US, such as heeling of some types of bone fractures such as non-unions.

Angiogenesis (Growth of Small Vessels for Sustaining Blood Circulation)

Reduced blood circulation in the extremities is a complicating factor for a series of diseases i.e. diabetes and psoriasis. It is also seen following excessive cigarette smoking, following a high plasma cholesterol concentration and hypertension. Sustaining synthesis of new vessels is essential for repairing such damaged areas, for wound healing and for generating new blood supply to i.e. bone tissue exposed to radiation therapy. It might also be an important factor for synthesis of new bone material.

In order to characterize the effect of PEMF on angiogenesis we used the previously developed model for testing angiogenesis in chicken embryos. Three days old fertilized eggs were cracked and chicken embryos with intact yolks were placed in plastic dishes. After three days of incubation at 37° C. in 3% $CO_2$, they were exposed to PEMF in a set up using three coils for a disc with one chicken embryo. The pulse generator applied + and −50 V with two phases (FIG. 8) and the distance between the egg and the coil surface was 4 cm. The temperature was thermostatically controlled in the incubator.

The synthesis of new blood vessels was analyzed by imaging techniques. The amount of new vessels (small capillaries) of a size from 10 micrometers to several hundred micrometers were evaluated by counting the number of new branches formed (FIG. 9, 701 and 702).

Figure 9:
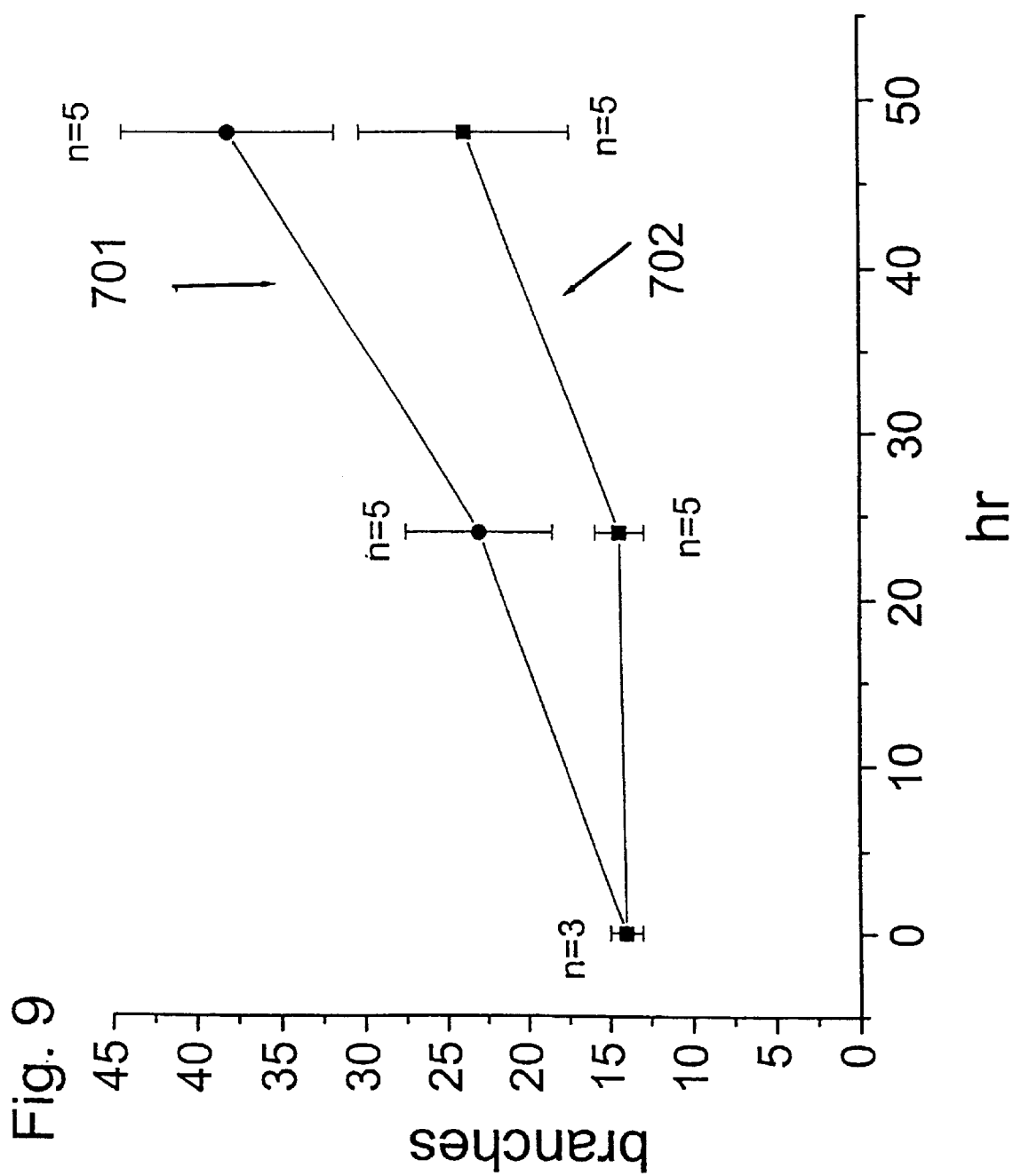
FIG. 9 illustrates the development of small capillaries in chicken embryos using the present invention.

FIG. 9 illustrates the number of branches at the small capillaries measured from a chicken embryo chorioallantoic membrane with and without exposure to PEMF using the device giving pulse currents as described in relation to FIG. 8. An image was taken of the membrane at the depicted time intervals and the number of branches at a 15 $mm^2$ area was counted either without (702) or with exposure to PEMF (701).

Figure 10A:
FIG. 10 illustrates images taken of a chicken embryo chorioallantoic membrane with (A) or without (B) exposure for 48 hr of PEMF.
Figure 10B:
Figure 11:
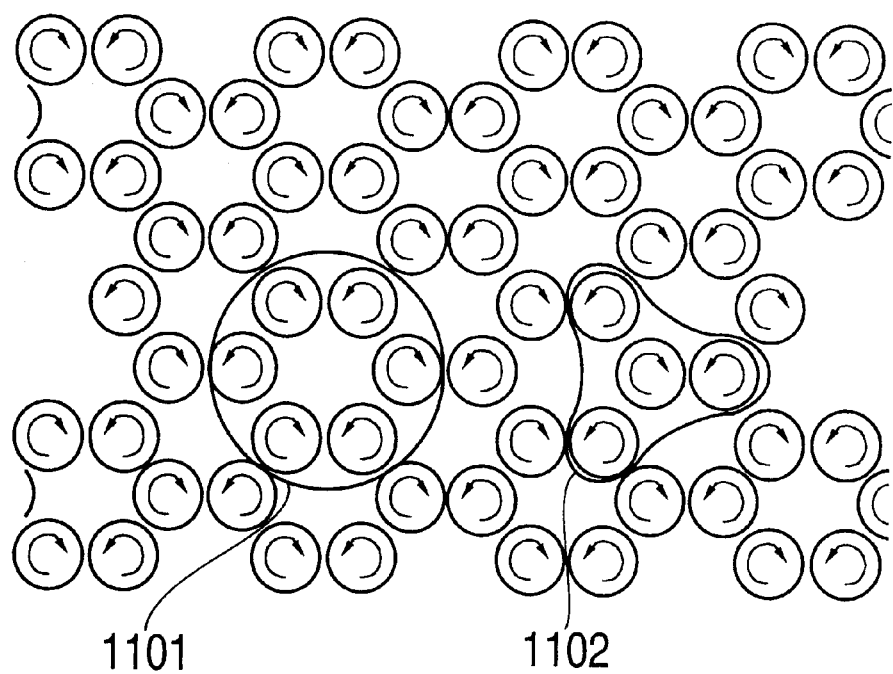
Figure 12:
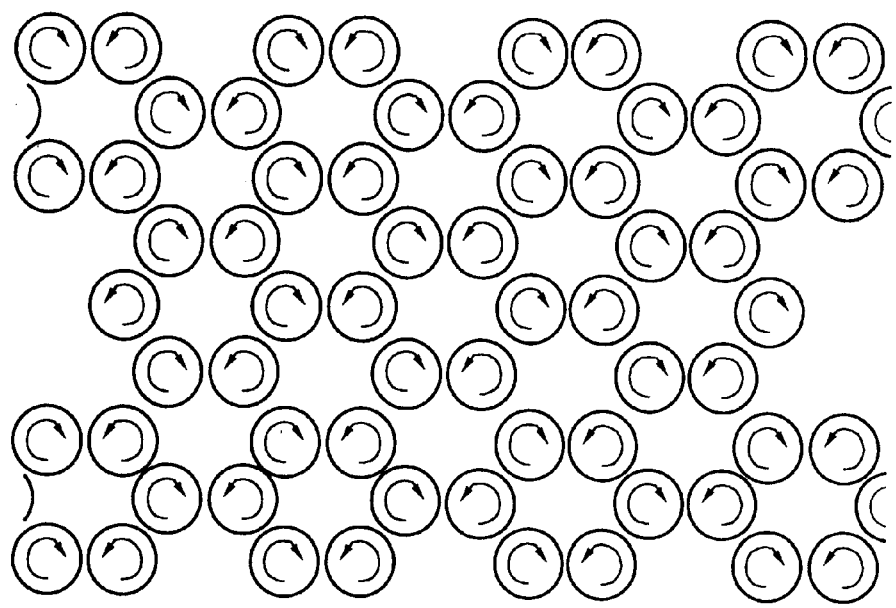

FIGS. 10A and 10B illustrate images taken of the chicken embryo chorioallantoic membrane with (A) or without (B) exposure to 48 hr of PEMF. Images were taken with a NIKON Cool Pix digital camera and images analysed by use of Adobe Photoshop software.

The FIGS. 10A and 10B show that it was possible to significantly enhance the number of new vessels synthesized as well as observe an enhanced rate of organization of the newly formed vessels (FIG. 10) using PEMF. These findings have important implications for initiating clinical research on wound healing and initiating attempts to enhance the blood circulation in patients suffering from i.e. diabetes. In addition patients with decomposed bone material due to radiation therapy can also benefit from treatment with this technology. Coils can be attached to the area in question and the bone material treated.

Treatment of Joints

The coils can be fastened to the area of treatment, i.e. the knee, where typically 4 coils are placed opposite each other as described in FIG. 5. They can be fastened to the knee using Velcro© material or a different type of trapping material, and the current supplied from wire attached to the pulse generator with 9–50 V battery or 12 or 50 V power supply from a transformer supported by 110 V or 220 V. This type of treatment can be conducted on both humans and animals, such as horses, suffering from injuries in joints.

Treatment of Dental Implants

For ingrowth of dental implants, a mask can be fitted to the jaws using 2 or more coils for each area being treated (FIG. 2). For this purpose we have constructed coils with a diameter of 25 mm described in the section: Construction of coils. A device can be fitted to the neck and head region of a person and thereby with an elastic material support the coils attached to the skin at the jaws. A particular problem in making implants is that after tooth extraction, there is usually a duration of several months before new bone material has grown into the area. The above-described device can accelerate this process. After insertion of the implant, treatment with pulsed electromagnetic fields can accelerate the growth of bone material onto the implant.

Small Fractures of the Hand

For fractures of small bones in the hand, the small 25 mm coils (in pairs) can be used also applying Velcro© material.

Treatment of Animals

Horses can be treated with pulsed electromagnetic fields using two or four coils as described in FIGS. 2–6, by strapping coils to the joint or to the area with a bone fracture by use of Velcro© material. A pulse generator with a 12–50 V power supply or a battery can be feeding pulses to the coils and be near the animal in a stable.

The Use of the Device for Treatment of Seeds

EXAMPLE 1

Laboratory Germination 600 grams standard calibrated and polished monogerm sugar beet seeds (CV Manhattan) were imbibed in water for two hours, dubbed on filter paper and incubated in a closed plastic bag at 4° C. for 17 hours. After this activation treatment, the seed lot was divided into 3 equal fractions and either left untreated or treated with PEMF for 90 min and PEMF for 240 min, followed by drying in an air stream overnight. The treated lots were then germinated in pleated paper boxes according to the ISTA-guidelines (International Rules for Seed Testing, Seed Sci. & Tech., 27, Suppl.; 1999) for sugar beet, but without pre-washing. Percent germination can be seen from table 1:

TABLE 1

Laboratory germination of naked sugar beet seed lots.

| Treatment | Germination, day 3 | Germination, day 4 | Germination, day 4, root length > 15 mm | Germination day 7 |
| --- | --- | --- | --- | --- |
| Untreated | 39 | 91 | 21 | 96 |
| PEMF, 90 min. | 59 | 95 | 29 | 97 |
| PEMF, 240 min. | 35 | 94 | 40 | 98 |

As can be seen from table 1, PEMF treatment enhances the speed of germination of pre-activated seeds in the parameter "4 day germination" with a root length of more than 15 mm, indicating enhanced vigor.

EXAMPLE 2

Effect of PEMF on Pelleted Seed

Three monogerm non-activated sugar beet varieties, Canaria, Manhattan and Marathon were standard pelleted and coated as for the Danish marked. Equally pelleted lots were then PEMF-treated at 25V and 55V respectively.

Controls were left untreated. After treatment, seed lots were analyzed for laboratory germination as well as field emergence in a standard split plot design with 3 varieties, 4 replications, 200 seeds/replication.

Percent laboratory germination and final field emergence (FE) is presented in table 2: All data given is an average of the 3 varieties.

TABLE 2

Laboratory germination and final FE (nr) of pelleted sugar beet seed lots.

| Treatment | Germination, day 4 | Germination, day 4, root length > 15 mm | Germination, day 7 | Pct. Final FE |
| --- | --- | --- | --- | --- |
| Untreated control | 72 | 0 | 96 | 86,0% (100) |
| 25V PEMF, 90 min. | 79 | 5 | 98 | 86,7% (101) |
| 50V PEMF, 90 min. | 74 | 4 | 99 | 86,9% (101) |

As can be seen from table 2, PEMF-treatment of pelleted seed lots enhances the number of seeds with a root length above 15 mm after 4 days of germination.

EXAMPLE 3

Effect of PEMF on Field Emergence of Naked Seed Lots

Three monogerm non-activated sugar beet varieties, Canaria, Manhattan and Marathon were PEMF-treated at 25V or 50V. Some seed lots were imbibed in water to a relative water content (RWC) on 30%, 45% and 65%, respectively, two hours before PEMF-treatment. Controls to PEMF-treatment were left untreated. After treatment, wet seed lots were air-dried. Seed lots were treated with thiram and mesurol and drilled for field emergence in a standard split plot design with 3 varieties, 4 replications, 200 seeds/replication. Successive seedling emergence was counted 3 times.

Field emergence data are given in table 3: All data given is average of 3 varieties.

TABLE 3

Field emergence data of naked sugar beet seed lots (HCPFE013):

| | Treatment | | | | | |
| --- | --- | --- | --- | --- | --- | --- |
| | Count 1 | | Count 2 | | Count 3 (final emergence) | |
| Pre-Treatment | Control | PEMF | Control | PEMF | Control | PEMF |
| | | 25V | | 25V | | 25V |
| Untreated | 27,9% | 28,6% (103) | 50,2% | 53,2% (106) | 80,5% | 83,8% (104) |
| 30% RWC | 29,0% | 29,7% (103) | 50,7% | 51,2% (101) | 83,2% | 82,4% (99) |
| 45% RWC | 27,8% | 29,3% (105) | 51,1% | 54,4% (107) | 82,3% | 82,2% (100) |
| 65% RWC | 29,1% | 29,4% (101) | 50,6% | 51,0% (101) | 82,5% | 81,5% (99) |
| | | 55V | | 55V | | 55V |
| Untreated | 27,9% | 27,3% (98) | 50,2% | 51,3% (102) | 80,5% | 82,2% (102) |

As will be seen from table 3, the PEMF treatment increases the speed of emergence (Count 2). In the final emergence (Count 3) PEMF has no effect if seed lots are pre-treated, whereas the non pre-treated naked seed lots gain from PEMF-treatment.

The Use of the Device for Treatment of Micro Organisms

Micro organisms, such as bacteria, can be treated with PEMF by which their survival can be improved under desirable conditions. It is an important technique to be able to code seeds with particular types of bacteria where after, when planted, a correct and not harmful environment supports germination and the formation of roots. Usually, the desirable bacteria are dried from containing 70% water to have only 20% water and subsequently be attached to the seeds. That, however, results in a strongly diminished survival rate of the bacteria, which has been a considerable problem. We have applied our apparatus, using the pulse pattern of FIG. 8, to improve the survival rate of the bacteria. It was done by exposing the bacteria for PEMF for two hours while being exposed to a procedure in which the water content was reduced from 70% to 40%. During this phase it is contemplated that particular intracellular proteins are synthesized (such as classes of heat shock proteins (hsp70)) whereby the bacteria are better withstanding the drying procedure. A subsequent addition of water and counting of colonies resulted in a 50 to 100 times better yield of bacteria when exposed to PEMF.

While the present invention is described herein with reference to illustrative embodiments for particular applications, it should be understood that the present invention is not limited thereto. Those having ordinary skill in the art and access to the teachings provided herein will recognize additional modifications, applications, and embodiments within the scope thereof and additional fields in which the invention would be of significant utility without undue experimentation. Thus, the scope of the invention should be determined by the appended claims and their legal equivalents, rather than by the examples given.

What is claimed is:

1. An apparatus adapted to stimulate and modulate a organism using pulsed electromagnetic fields, the apparatus comprising:

a plurality of electrically conducting coils each having a center axis, each center axis being directed into said living organism; and a pulse generator operationally connected to said coils for supplying a series of current pulses for conduction in said coils, said series of current pulses being adapted to generate a periodically varying magnetic field from each of said coils for inducing an electrical field, a number of said coils being arranged in a honeycomb configuration comprising a first coil and three coils adjacent to the first coil, whereby for a given current pulse supplied by the pulse generator, a magnetic field at a center of the first coil is directed toward the living organism and magnetic fields at centers of the three coils are directed away from the living organism.

2. An apparatus according to claim 1, wherein said coils each have a part being at least substantially perpendicular to a central axis of the respective coil and facing the living organism, the parts of the coils being positioned in one or more planes each comprising a plurality of coil parts.

3. An apparatus according to claim 2, wherein at least one of the coils having a part within a predetermined area has a center to center distance to a nearest coil being between 1D–1.5D, where D is a diameter of the at least one coil.

4. An apparatus according to claim 1, further comprising a flat sheet of flexible material for at least partly surrounding the living organism, in which the plurality of coils are embedded.

5. An apparatus according to claim 1, comprising sets of the coils being arranged in the honeycomb configuration and positioned on at least substantially opposite sides of the living organism and having at least substantially coincident central axes.

6. An apparatus according to claim 1, wherein for the given current pulse supplied by the pulse generator, the first coil conducts the current pulse in a clockwise direction and the three coils conduct the current pulse in a counter-clockwise direction taken along central axes of the first coil and the three coils, respectively, in a direction toward the living organism.

7. An apparatus according to claim 1, wherein said coils have a ratio between inductance and resistance to provide a pulsed current with a rise time in a range from 0.1 ms to 2 ms and a maximum current corresponding to a maximum magnetic field of 0.05–0.1 Tesla at the centers of the coils.

8. An apparatus according to claim 1, wherein the pulse generator is adapted to generate current pulses with a frequency in a range from 1 to 300 Hz.

9. An apparatus according to claim 1, further comprising a power supply which supplies power to the pulse generator, the power supply being a battery within the apparatus that supplies an electric potential of 50 V or less.

10. An apparatus according to claim 1, wherein the pulse generator comprises a CMOS circuit.

11. An apparatus according to claim 1, wherein the coils and the pulse generator provide a series of pulses forming a temporal overlap between the periodically varying magnetic fields from the coils to form a periodically varying total magnetic field having a frequency in a range from 1 to 1000 Hz.

12. An apparatus according to claim 1, wherein cross sections of the coils, perpendicularly to central axes, are at most 100 cm$^2$.

13. An apparatus according to claim 1, the apparatus being adapted to be carried by a person during operation.

14. An apparatus according to claim 1, further comprising a fastener which fastens the coils to a body part of the living organism.

15. The apparatus according to claim 1, wherein the coils are positioned adjacently to the living organism, whereby the apparatus enhances tissue growth.

16. The apparatus according to claim 15, wherein the series of pulses and the coils are adjustable so that maximum regions of induced electrical fields in a predetermined portion of the living organism are sufficiently small so as not to elicit action potentials in cells thereof.

17. The apparatus according to claim 15, whereby the living organism is a human or an animal, and the coils are positioned at a jaw of the human or the animal for inducing enhanced bone growth.

18. The apparatus according to claim 15, whereby the living organism is a human or an animal, and the coils are positioned at a jaw of the human or the animal for promoting in-growth of dental implants.

19. The apparatus according to claim 15, whereby the living organism is a human or an animal, and the coils are attached to a joint region of the human or the animal for treatment of arthritis or pain, or for promoting growth of bone, cartilage or blood vessels.

20. The apparatus according to claim 15, whereby the living organism is a human or an animal, and the coils are attached to a joint region of the human or animal to prevent arthritis or pain, or to promote bone growth after a bone fracture.

21. The apparatus according to claim 15, wherein the pulse generator is operated for a period of time exceeding 15 minutes.

22. The apparatus according to claim 1, whereby the living organism comprises micro organisms, living cells, or tissue, the coils being positioned adjacently thereto.

23. The apparatus of claim 1, wherein the living organisms are micro-organisms and central axes of the coils are directed into the micro-organisms.

24. An apparatus of claim 1, wherein the living organism comprises seeds, plants or plant tissue, central axes of the coils being directed into the seeds, plants or plant tissue.

25. An apparatus according to claim 1, wherein the pulse generator provides a delay of 0.01–10 ms between adjacent current pulses for the coils.

26. An apparatus according to claim 1, wherein the pulse generator provides the current pulses as having a time duration of 1–100 ms.

27. An apparatus according to claim 1, the apparatus being adapted to operate for a period of time exceeding 15 minutes.

28. A method for treating a living organism with pulsating electromagnetic fields, the method comprising:

providing a plurality of coils each having a central axis directed into the living organism; and providing a series of current pulses to the coils, said series of pulses generating a periodically varying magnetic field from the coils for inducing an electrical field, the coils being provided in a honeycomb configuration comprising a first coil and three coils adjacent to the first coil, whereby for a given current pulse of the series of current pulses, a magnetic field at a center of the first coil is directed toward the living organism and magnetic fields at centers of the three coils are directed away from the living organism.

29. A method according to claim 28, wherein said providing the coils comprises providing each of the coils as having a part arranged at least substantially perpendicular to a center axis of the respective coil to face the living organism, in one or more planes each comprising a plurality of coil parts.

30. A method according to claim 29, wherein said providing the coils comprises providing at least one of the coils as having a part within a predetermined area and having a center to center distance to a nearest coil between 1D–1.5D, where D is a diameter of the at least one coil.

31. A method according to claim 28, further comprising embedding the plurality of coils in a flat sheet of flexible material and at least partly surrounding the living organism with the flat sheet.

32. A method according to claim 28, wherein, for the given current pulse provided, the first coil conducts the current pulse in a clockwise direction and the three coils conduct the current pulse in a counter-clockwise direction taken along central axes of the first coil and the three coils, respectively, in a direction toward the living organism.

33. A method according to claim 28, wherein the coils are provided with a pulsed current having a rise time in a range from 0.1 ms to 2 ms and a maximum current to provide a magnetic field of 0.01 Tesla at the centers of the coils.

34. A method according to claim 28, wherein the current pulses are provided with a frequency in a range from 1 to 300 Hz.

35. A method according to claim 28, wherein a pulse generator provides the current pulses, and wherein the pulse generator and the coils are provided in an apparatus, the method further comprising providing a power supply for supplying power to the pulse generator, the power supply being a battery within the apparatus that supplies an electric potential of 50 V or less.

36. A method according to claim 28, wherein the coils are provided with a series of current pulses forming a temporal overlap between the varying magnetic fields from the coils to form a periodically varying total magnetic field having a frequency in a range from 1 to 1000 Hz.

37. A method according to claim 28, wherein said providing the coils comprises providing coils having cross section, perpendicularly to center axes thereof, of at most 100 cm$^2$.

38. A method according to claim 28, further comprising fastening the coils to a body part of a human or an animal.

39. A method according to claim 28, whereby the living organism comprises cells, micro organisms or tissue.

40. A method according to claim 28, wherein the series of current pulses and the coils are adjustable so that maximum regions of induced electrical fields in a predetermined portion of the living organism is sufficiently small so as not to elicit action potentials in cells of the living organism.

41. A method according to claim 28, wherein the living organism is a human or an animal, the method further comprising positioning the coils at a jaw of the human or the animal for inducing enhanced bone growth.

42. A method according to claim 28, wherein the living organism is a human or an animal, the method further comprising positioning the coils at a jaw of the human or the animal for promoting in-growth of dental implants.

43. A method according to claim 28, wherein the living organism is a human or an animal, the method further comprising attaching the coils to a joint region of the human or the animal for treatment of arthritis or pain, or for promoting growth of bone, cartilage or blood vessels.

44. A method according to claim 28, wherein the living organism is a human or an animal, the method further comprising attaching the coils to a joint region of the human or the animal to prevent arthritis or pain or to promote bone growth after a bone fracture.

45. A method according to claim 28, whereby the living organism comprises micro-organisms, the method further comprising positioning the coils adjacently to the micro-organisms, to treat the micro-organisms.

46. A method according to claim 28, wherein the living organism comprises seeds, plants or plant tissue, the method further comprising positioning the coils adjacently to the seeds, plants or plant tissue.

47. A method according to claim 28, further comprising providing a delay of 0.01–10 ms between adjacent current pulses for the coils.

48. A method according to claim 28, further comprising providing the current pulses having a time duration of 1–100 ms.

49. A method according to claim 28, the method comprising providing pulses for the coils for a period of time exceeding 15 minutes.

* * * * *